US010617703B2

(12) United States Patent
Ray, II

(10) Patent No.: US 10,617,703 B2
(45) Date of Patent: *Apr. 14, 2020

(54) COMPOSITIONS AND METHODS FOR TREATING AN INFECTION

(71) Applicant: CMPD LICENSING, LLC, Conroe, TX (US)

(72) Inventor: Jay Richard Ray, II, Conroe, TX (US)

(73) Assignee: CMPD LICENSING, LLC, Conroe, TX (US)

(*) Notice: Subject to any disclaimer, the term of this patent is extended or adjusted under 35 U.S.C. 154(b) by 67 days.

This patent is subject to a terminal disclaimer.

(21) Appl. No.: 15/668,449

(22) Filed: Aug. 3, 2017

(65) Prior Publication Data
US 2017/0333464 A1 Nov. 23, 2017

Related U.S. Application Data

(63) Continuation-in-part of application No. 15/597,936, filed on May 17, 2017, now Pat. No. 10,105,342, and a continuation-in-part of application No. 14/566,313, filed on Dec. 10, 2014, now abandoned, said application No. 15/597,936 is a continuation-in-part of application No. 15/440,800, filed on Feb. 23, 2017, and a continuation-in-part of application No. 14/975,172, filed on Dec. 18, 2015, now Pat. No. 9,707,229, and a continuation-in-part of application No. 14/819,342, filed on Aug. 5, 2015.

(60) Provisional application No. 62/298,994, filed on Feb. 23, 2016, provisional application No. 62/298,991, filed on Feb. 23, 2016.

(51) Int. Cl.
A61K 31/7036 (2006.01)
A61K 31/7056 (2006.01)
A61K 31/5383 (2006.01)
A61K 9/00 (2006.01)
A61K 9/14 (2006.01)
A61K 9/08 (2006.01)
A61K 38/12 (2006.01)
A61K 31/351 (2006.01)
A61K 9/48 (2006.01)
A61K 9/06 (2006.01)
A61K 45/06 (2006.01)
A61K 31/65 (2006.01)
A61K 31/7048 (2006.01)
A61K 31/431 (2006.01)
A61K 31/506 (2006.01)
A61K 31/496 (2006.01)

(52) U.S. Cl.
CPC ........ *A61K 31/7036* (2013.01); *A61K 9/0014* (2013.01); *A61K 9/0019* (2013.01); *A61K 9/0043* (2013.01); *A61K 9/06* (2013.01); *A61K 9/08* (2013.01); *A61K 9/14* (2013.01); *A61K 9/48* (2013.01); *A61K 31/351* (2013.01); *A61K 31/431* (2013.01); *A61K 31/496* (2013.01); *A61K 31/506* (2013.01); *A61K 31/5383* (2013.01); *A61K 31/65* (2013.01); *A61K 31/7048* (2013.01); *A61K 31/7056* (2013.01); *A61K 38/12* (2013.01); *A61K 45/06* (2013.01)

(58) Field of Classification Search
CPC .............. A61K 31/7036; A61K 31/496; A61K 31/506; A61K 9/0043; A61K 31/431; A61K 31/7048; A61K 31/65; A61K 45/06; A61K 9/06; A61K 9/0019; A61K 9/08; A61K 9/0014; A61K 9/48; A61K 9/14; A61K 31/5383; A61K 31/351; A61K 31/7056; A61K 38/12
See application file for complete search history.

(56) References Cited

U.S. PATENT DOCUMENTS

| 2002/0061281 | A1 | 5/2002 | Osbakken et al. |
| 2003/0143162 | A1 | 7/2003 | Speirs et al. |
| 2009/0016990 | A1 | 1/2009 | Alberte et al. |
| 2012/0328671 | A1 | 12/2012 | O'Neil et al. |
| 2013/0072563 | A1* | 3/2013 | Ho .................. A61L 2/186 514/557 |
| 2014/0256826 | A1 | 9/2014 | Lemire et al. |

FOREIGN PATENT DOCUMENTS

WO   2006060027   6/2006

OTHER PUBLICATIONS

Roerig, "Diflucan-fluconazole tablet, Diflucan-fluconazole powder, for suspension," Pfizer, Mar. 2013, document of 61 pages.
PCCA, "LoxaSperse™, Powder Excipient Base for Use in Nebulization and Irrigation Compounds," 2013, document of 3 pages.
Pfizer, "Fluconazole Injection, USP, in INTRAVIA Plastic Container," Pfizer Injectables, Aug. 2010, document of 4 pages, https://www.pfizer.com/files/products/uspi_fluconazole.pdf.
PCCA XYIFOS Trademark Appl. No. 8842712 (May 27, 2015), pp. 1-8.
Freels, Lexington Podiatry (2011), pp. 1-2.
PCCA Science, "Technical Report: The Antimicrobial Activity of Itraconazole and LoxaSperse TM Against Biofilms of C. albicans," 2013, www.ccarx.com, pp. 1-2.
U.S. Appl. No. 14/819,342, filed Aug. 5, 2015, Applicant is CMPD Licensing, LLC, Inventor is Jay Richard Ray, II.
Label for DIFLUCAN (Fluconazole Tablets), Distributed by Roerig, a Division of Pfizer, Mar. 2013 (35 pages).
Label (Package Insert) for Azithromycin, Distributed by SICOR Pharmaceuticals, Inc., Dec. 2016 (18 pages).

(Continued)

Primary Examiner — Sarah Pihonak
Assistant Examiner — Jason Deck
(74) Attorney, Agent, or Firm — Akerman LLP

(57) ABSTRACT

The present application relates to compounded compositions, methods of making compounded compositions, and methods of using compounded compositions. For example, disclosed herein are compounded compositions and methods of making compounded compositions comprising one or more anti-infective agents such as mupirocin.

9 Claims, No Drawings

(56) References Cited

OTHER PUBLICATIONS

Label for BACTROBAN (mupirocin), Distributed by GlaxoSmithKline, Dec. 2015 (10 pages).
PCCA, Brochure for LoxaSperse, "Powder Excipient Base for Use in Nebulization and Irrigation Compounds", 2013 (3 pages).
PCCA, "New, Exclusive PCCA Base, XyliFos™: Boost the LoxaSperse™ Power in Nasal Nebulization and Decrease your Cost", Aug. 7, 2015 (2 pages).
Medinvent, "The NasoNeb Nasal Nebulizer", Nov. 15, 2013.

* cited by examiner

COMPOSITIONS AND METHODS FOR TREATING AN INFECTION

CROSS-REFERENCE TO RELATED APPLICATIONS

The present application is a continuation-in-part application of U.S. patent application Ser. No. 15/597,936, filed 17 May 2017, and U.S. patent application Ser. No. 14/566,313, filed 10 Dec. 2014, each of which is incorporated by reference in its entirety. U.S. patent application Ser. No. 15/597,936 is a continuation-in-part application of U.S. patent application Ser. No. 15/440,800, filed 23 Feb. 2017, U.S. patent application Ser. No. 14/975,172, filed 18 Dec. 2015, and U.S. patent application Ser. No. 14/819,342, filed 5 Aug. 2015, each of which is incorporated by reference in its entirety. U.S. patent application Ser. No. 15/440,800 claims priority to U.S. Provisional Patent Application No. 62/298,991, filed 23 Feb. 2016, and to U.S. Provisional Patent Application No. 62/298,994, filed 23 Feb. 2016, each of which is incorporated by reference in its entirety.

BACKGROUND

The body normally serves as host for a variety of bacteria and fungi. Most of the time, the balance between the body as host and the microorganisms is maintained. However, there are times when the physiological, biochemical, and/or environmental conditions permit the microorganisms to tip that balance, thereby causing an infection.

Despite advances in the understanding of the pathology of bacterial infections and fungal infections, there is still a need for compositions and methods that efficiently treat or prevent the progression and reoccurrence of bacterial infections and fungal infections that affect the skin, the respiratory system, or the feet.

SUMMARY

In one aspect, a method of treating or preventing a bacterial infection of a subject includes formulating a treatment composition comprising combining a diluent and a dry powder, wherein the dry powder comprises one or more anti-infective agents including at least a first anti-infective agent comprising streptomycin. The method may also include contacting a body surface of a subject that is infected or suspected to be infected with the treatment composition to topically deliver the one or more anti-infective agents to the body surface.

In various embodiments, the one or more anti-infective agents comprise a second anti-infective agent comprising colistimethate, clindamycin, mupirocin, levofloxacin, or combination thereof. Formulating the treatment composition may further include opening a capsule comprising at least the first anti-infective agent to release the dry powder of at least the first anti-infective agent for combining with the diluent. The capsule may include a dry powder including both the first anti-infective agent and the second anti-infective agent. In one embodiment, the compounded composition comprises between about 1% and about 10% streptomycin by weight. Contacting the body surface of the subject may include contacting the body surface with a suitable amount of the treatment composition to topically deliver between 25 mg and 1 gm of streptomycin per day.

In various embodiments, the second anti-infective agent is present in the dry powder at a ratio between about 1:3 and about 1:10 with respect to the first anti-infective agent. In one example, the diluent comprises a cream, ointment, emulsion, or gel. In one configuration, the diluent comprises a sterile aqueous solution, and contacting the body surface comprises nebulizing the treatment composition to deliver the streptomycin to a surface of a lung of the subject. In another example, the diluent comprises a sterile aqueous solution, and contacting the body surface comprises nebulizing the treatment composition to deliver the streptomycin to a surface of a lung of the subject. In one example, the body surface comprises broken tissue, the diluent is a sterile aqueous diluent, and the treatment composition comprises a wound irrigation solution. In another example, the body surface comprises broken tissue, the diluent comprises a dry powder diluent, and the treatment composition comprises a wound powder. In one example, the diluent comprises an aqueous solution and contacting the body surface comprises contacting foot of the subject with the treatment composition in a foot bath.

In one embodiment, combining the diluent and dry powder comprises combining a dry powder of streptomycin sulfate for injection with the diluent. In another embodiment, formulating the treatment composition further comprises combining an additional anti-infective agent comprising a mupirocin ointment with the dry powder and diluent.

In another aspect, a homogenous compounded ointment for the treatment or prevention of a bacterial infection of a subject treatment includes streptomycin sulfate for injection in an ointment base and the compounded ointment comprises between about 1% and 10% streptomycin by weight.

In various embodiments, the compounded ointment further comprising an additional anti-infective agent comprising an antibacterial, antifungal, or combination thereof. The additional anti-infective agent may include colistimethate, clindamycin, mupirocin, levofloxacin, or combination thereof. In one example, the additional anti-infective agent is present in the compounded ointment at a weight ratio between about 1:3 and about 1:10 with respect to the streptomycin of the streptomycin sulfate.

In still another aspect, a kit for treating or preventing a bacterial infection of a subject may include a capsule containing a dry powder including at least streptomycin sulfate for injection and a diluent for combining with the dry powder to formulate a topical treatment composition to administer to a body surface that is infected or suspected to be infected. The dilute may comprise an ointment, cream, gel, emulsion, aqueous solution, or powder.

In one embodiment, the kit comprises an amount of dry powder and diluent for preparation of a suitable amount of treatment composition to topically deliver between 25 mg and 1 gm of streptomycin in one day. In various embodiments, the dry powder further includes an additional anti-infective agent comprising colistimethate, clindamycin, mupirocin, levofloxacin, or combination thereof. In one example, the additional anti-infective agent is present in the dry powder at a weight ratio between about 1:3 and about 1:10 with respect to streptomycin of the streptomycin sulfate. In another example, the diluent may include a sterile aqueous solution, and the topical treatment composition may comprise a nebulization solution to deliver the streptomycin and additional anti-infective to a surface of a lung of the subject. In still another example, the diluent may comprise a sterile aqueous solution, and the topical treatment composition comprises a wound irrigation solution to deliver the streptomycin and additional anti-infective to a broken tissue surface of the subject. In yet another example, the diluent comprises a dry powder and the topical treatment composition comprises a wound powder. In still yet another example, the diluent comprises an aqueous solution and the topical treatment composition a foot bath solution.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

A. Definitions

As used in the specification and the appended claims, the singular forms "a", "an", and "the" include plural referents unless the context clearly dictates otherwise.

The phrase "consisting essentially of" limits the scope of a claim to the recited components in a composition or the recited steps in a method as well as those that do not materially affect the basic and novel characteristic or characteristics of the claimed composition or claimed method. The phrase "consisting of" excludes any component, step, or element that is not recited in the claim. The phrase "comprising" is synonymous with "including", "containing", or "characterized by", and is inclusive or open-ended. "Comprising" does not exclude additional, unrecited components or steps.

As used herein when referring to any numerical value, the term "about" means a value falling within a range that is ±10% of the stated value.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein, the terms "optional" or "optionally" means that the subsequently described event or circumstance can or cannot occur, and that the description includes instances where said event or circumstance occurs and instances where it does not. In an aspect, a disclosed method can optionally comprise one or more additional steps, such as, for example, repeating an administering step or altering an administering step.

As used herein, the term "subject" refers to the target of administration, e.g., a human being. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, or rodent. The term does not denote a particular age or sex. Thus, adult and child subjects, as well as fetuses, whether male or female, are intended to be covered. In an aspect, a subject can be a human patient. In an aspect, the subject can have diabetes, can be obese, can be immunocompromised, can be non-ambulatory, or can have poor blood flow, or a combination thereof. In an aspect, the subject can routinely wear thick socks or wear heavy boots. In an aspect, the subject can have been diagnosed with or can be suspected of having (i) cancer that affects at least a part of the respiratory tract, (ii) emphysema, (iii) pneumonia, (iv) bronchitis, (v) tuberculosis, (vi) asthma, or (vii) a combination thereof.

A subject can have a bacterial infection, be suspected of having a bacterial infection, or be at risk of developing a bacterial infection. A subject can have a fungal infection, be suspected of having a fungal infection, or be at risk of developing a fungal infection. A subject can have a bacterial infection and a fungal infection, be suspected of having a bacterial infection and a fungal infection, or be at risk of developing a bacterial infection and a fungal infection.

For example, a subject at risk of developing a bacterial infection can have, for example, risk factors for developing a bacterial infection (e.g., have damaged or moist skin, have a chronic disease, and/or be immunocompromised). For example, a subject at risk for developing a bacterial infection can be exposed to a bacterium or bacteria due to employment (e.g., a health care worker) or due to the prevalence of a bacterium or bacteria at a specific location (e.g., a hospital).

For example, a subject at risk of developing a fungal infection can have, for example, risk factors for developing a fungal infection (e.g., have damaged or moist skin, have a chronic disease, and/or be immunocompromised). For example, a subject at risk for developing a fungal infection can be exposed to a fungus or fungi due to employment (e.g., a health care worker) or due to the prevalence of a fungus or fungi at a specific location (e.g., a hospital).

A "patient" refers to a subject afflicted with one or more infections. In an aspect, a patient can refer to a subject that has been diagnosed with or is suspected of having a bacterial infection. In an aspect, a bacterial infection or suspected bacterial infection can affect at least a portion of one or both feet of the subject, the subject's skin, the subject's respiratory system, or another appendage, such as at least a portion of one or both of the subject's hands. In an aspect, a patient can refer to a subject that has been diagnosed with or is suspected of having a fungal infection. In an aspect, a fungal infection or suspected fungal infection can affect at least a portion of one or both feet of the subject, the subject's skin, the subject's respiratory system, or another appendage, such as at least a portion of one or both of the subject's hands.

As used herein, the term "treatment" refers to the medical management of a patient with the intent to cure, ameliorate, stabilize, or prevent a disease, pathological condition, or disorder (such as, for example, a bacterial infection, a suspected bacterial infection, a fungal infection, or a suspected fungal infection, or both). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

In an aspect, "treating" means eradicating a bacterial infection, a fungal infection, a suspected bacterial infection, a suspected fungal infection, or a combination thereof. In an aspect, treating means reducing the effects of a bacterial infection or a fungal infection or symptoms of a bacterial infection or a fungal infection. For example, treating an infection can reduce the severity of an established infection in a subject by 1%-100% as compared to a control. In an aspect, treating can refer to a 1%, 2%, 3%, 4%, 5%, 6%, 7%, 8%, 9%, 10%, 20%, 30%, 40%, 50%, 60%, 70%, 80%, 90%, or 100% reduction in the severity of an established bacterial infection or an established fungal infection. For example, treating an infection can reduce one or more symptoms of an infection in a subject by 1%-100% as compared to a control. In an aspect, treating can refer to 1%, 2%, 3%, 4%, 5%, 6%, 7%, 8%, 9%, 10%, 20%, 30%, 40%, 50%, 60%, 70%, 80%, 90%, 100% reduction of one or more symptoms of an established bacterial infection or an established fungal infection. It is understood that treatment does not necessarily refer to a cure or complete ablation or eradication of the bacterial infection, the fungal infection, or both. However, in an aspect, treatment can refer to a cure or complete ablation or eradication of the bacterial infection, the fungal infection, or both.

As used herein, the term "prevent" or "preventing" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed. In an aspect, preventing a bacterial infection, fungal infection, or both is intended.

As used herein, the term "diagnosed" means having been subjected to a physical examination by a person of skill, for example, a physician, and found to have a condition that can be diagnosed or treated by the disclosed compounded composition or the disclosed methods. For example, "diagnosed with a bacterial infection" means having been subjected to a physical examination by a person of skill, for example, a physician, and found to have a condition that can be treated by a disclosed compounded composition or a disclosed method. For example, "suspected of having a bacterial infection" can mean having been subjected to a physical examination by a person of skill, for example, a physician, and found to have a condition that can likely be treated by a disclosed compounded composition or a disclosed method. For example, "diagnosed with a fungal infection" means having been subjected to a physical examination by a person of skill, for example, a physician, and found to have a condition that can likely be treated by a disclosed compounded composition or a disclosed method. For example, "suspected of having a fungal infection" can mean having been subjected to a physical examination by a person of skill, for example, a physician, and found to have a condition that can be likely be treated by a disclosed compounded composition or a disclosed method.

As used herein, the terms "administering" and "administration" refer to any method of providing a disclosed compounded composition or a pharmaceutical preparation comprising a disclosed compounded composition to a subject. Such methods are well known to those skilled in the art and include, but are not limited to: oral administration, transdermal administration, administration by inhalation, nasal administration, topical administration, intravaginal administration, ophthalmic administration, intra-aural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a disclosed compounded composition, or anti-infective agent can be administered therapeutically; that is, administered to treat an existing disease or condition. In further various aspects, a disclosed compounded composition or a pharmaceutical preparation comprising a disclosed compounded composition can be administered prophylactically; that is, administered for prevention of a disease or condition. In an aspect, the skilled person can determine an efficacious dose, an efficacious schedule, and an efficacious route of administration for a disclosed compounded composition or a disclosed pharmaceutical preparation comprising a disclosed compounded composition so as to treat or prevent an infection. In an aspect, the skilled person can also alter, change, or modify an aspect of an administering step so as to improve efficacy of a disclosed compounded composition or a disclosed pharmaceutical preparation comprising a disclosed compounded composition. In an aspect, administering means contacting at least a portion of one foot or both feet of a subject with agitated water comprising a disclosed compounded composition or a disclosed pharmaceutical preparation comprising a disclosed compounded composition. In an aspect, administering means contacting at least a portion of the subject's skin with disclosed compounded composition or a disclosed pharmaceutical preparation comprising a disclosed compounded composition. In an aspect, administering means contacting at least a portion of the subject's respiratory system with a disclosed compounded composition or a disclosed pharmaceutical preparation comprising a disclosed compounded composition. In an aspect, administering means contacting at least a portion of one foot or both feet of a subject with agitated water comprising a solution or suspension comprising a disclosed compounded composition. In an aspect, administering means contacting at least a portion of the subject's skin with a solution or suspension comprising a disclosed compounded composition. In an aspect, administering means contacting at least a portion of the subject's respiratory system with a solution or suspension comprising a disclosed compounded composition.

As used herein, a "foot bath" refers to a container that can hold some volume (e.g., about 1.0 liters to about 10 liters) of an aqueous solution or suspension (e.g., water) and is designed to physically accommodate at least a portion of one or both feet of a subject. Foot baths are known to the skilled person. A foot bath can comprise several features or agents that effect various functions. For example, a foot bath can comprise one or more lights or light-emitting devices, a mechanical agitation agent (e.g., one or more jets or bubble makers) to physically agitate the enclosed water, a bubble agent to create bubbles within the enclosed water, a heating agent to heat the enclosed water, a vibration agent to vibrate the enclosed water (e.g., a high frequency vibration massage), an infrared device to provide infrared light to a foot or feet of the subject, a massage agent (e.g., a roller) that provides massaging contact to at least a portion of one or both feet, a pedicure agent that can clean or contact a foot or feet with a pumice, or a combination thereof. In an aspect, a foot bath can have a water fall element. In an aspect, an agitation agent or an agitator can be coupled to both a motor and the foot bath. Motors and agitators are known to the art. In an aspect, a foot bath can comprise one or more splash guards and other spill-resistant features to ensure that the water remains enclosed within a container. A foot bath may also accommodate a subject's calves, meaning that the container is "deep" so as to allow the enclosed water to contact both the feet and at least a portion of the calves of the subject. Several manufacturers market foot baths including PIBB, Dr. Scholl's, Kendal, Conair (e.g., Model FB5X, FB3, FB27R, FB30, FB52, etc.), and Brookstone.

As used herein, a "mixing container" can be a container that can accommodate one more liquids (such as a diluent, for example) and one or more disclosed compounded compositions or disclosed anti-infective agents. A mixing container can have a lid or a cover, which facilitates the mixing of any liquid with any solid that has been added to the container. A mixing container can be used to generate a solution or suspension. In an aspect, a mixing container can contain about 2 ounces to about 30 ounces. In an aspect, a mixing container can contain about 6 ounces. In an aspect, a mixing container can contain about 16 ounces. The art is familiar with mixing containers and mixing containers are commercially available.

As used herein, "modifying the method" can comprise modifying or changing one or more features or aspects of one or more steps of a disclosed method. For example, in an aspect, a method can be altered by changing the amount of a disclosed compounded composition applied to a subject's skin, or by changing the frequency of the subject's use of the compounded composition, or by changing the duration of time that the subject uses the compounded composition, or a combination thereof. In an aspect, a method can be altered by changing the amount of a disclosed compounded composition added to a foot bath, by changing the frequency of the subject's use of the foot bath, or by changing the duration of time that the subject's foot or feet contact the water contained within the foot bath, or a combination thereof. The same modifications can be applied to a method comprising intranasally administering a disclosed compounded composition or a disclosed pharmaceutical preparation comprising a disclosed compounded composition to the subject's nares or topically administering a disclosed compounded composition or a disclosed pharmaceutical preparation comprising a disclosed compounded composition to the subject's skin.

The term "contacting" as used herein refers to bringing at least one disclosed compounded compositions or a disclosed pharmaceutical preparation comprising a disclosed compounded composition together with a target area or intended target area in such a manner that the disclosed compounded composition or the disclosed pharmaceutical preparation comprising a disclosed compounded composition can exert an effect on the intended target or targeted area either directly or indirectly. A target or intended target area can be at least a portion of one or both feet of a subject or at least portion of the subject's skin or an area diagnosed with, suspected of having a bacterial infection or a fungal infection, or susceptible to developing a bacterial infection or a fungal infection. In an aspect, "contacting" means to insert or immerse at least a portion of one or both feet of a subject into the water contained within a foot bath. In an aspect, "contacting" means topically applying a disclosed compounded composition to the skin of a subject or intranasally administering a disclosed compounded composition to the nares of a subject.

The term "mixing" as used in a disclosed method means to physically combine the recited components so as to achieve a homogenous compounded composition (which, for example, can be a dry powder formulation or an ointment). In an aspect, the recited components can be shaken, or stirred, or agitated so as to achieve a homogenous compounded composition. In an aspect, "mixing" can also include sifting the homogenous compounded composition though a fine mesh strainer. A suitable mixer is a TURBULA® mixer, which is able to mix powdery substances with differing specific weights and particle sizes. The mixing can be generally performed for a pre-determined amount of time, i.e., for 10 seconds, 20 seconds, 30 seconds, 45 seconds, 1 minute, 5 minute, 10 minutes, 20 minutes, 30 minutes, 40 minutes, 50 minutes, 1 hour, 2 hours, 3 hours, or more. A person skilled in the art could ascertain without undue experimentation, the amount of time required to mix the recited components so as to achieve a homogenous compounded composition. In an aspect, mixing a powder and an ointment may include combining one or more powders and the ointment. One or more of the powders or portions thereof may be wetted prior to addition to the ointment. Thus, in an aspect, adding, combining, or mixing a powder and an ointment may include adding, combining, or mixing wetted powder and the ointment.

In an aspect, "mixing" can be used to describe the process of making a solution or suspension by adding one or more disclosed compounded compositions to a diluent. For example, mixing means to physically combine a disclosed compounded composition with a diluent to make a solution or a suspension. Such mixing can occur in a disclosed mixing container.

As used herein, "ointment" refers to a homogeneous, viscous preparation that can be applied to a subject. In aspect, the term "ointment" can be considered synonymous to a lotion, a cream, an emulsion, a gel, an emollient, etc. In an aspect, an ointment comprises a disclosed compounded composition. An ointment can be applied in a variety of ways, included, for example, but not limited to, direct topical application to the subject's skin or contact with skin in an enclosed environment, such as a foot bath.

As used herein, LoxaSperse™ refers to an excipient base powder comprising a blend of micronized xylitol and poloxamers. Such base compositions are known to those skilled in the art. LoxaSperse™ is manufactured by PCCA (Houston, Tex.) and is used as a chemical dispersing or solubilizing agent, thereby improving the solubility and dispersibility of poorly water soluble active pharmaceutical ingredients (APIs) or agents. LoxaSperse™ can be obtained from a bulk source.

As used herein, XyliFos™ refers to an excipient base powder comprising xylitol, poloxamer 407, hydroxylpropyl betadex, and epigallocatechin gallate. XyliFos™ is manufactured by PCCA (Houston, Tex.) and is used as a chemical dispersing or solubilizing agent, thereby improving the solubility and dispersibility of poorly water soluble active pharmaceutical ingredients (APIs) or agents. XyliFos™ can be obtained from a bulk source.

In an aspect, xylitol can comprise an ointment or can comprise a dry powder. In an aspect, xylitol can be xylitol NF (20-80 MESH).

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier" refers to sterile aqueous or nonaqueous solutions, or suspensions, which may include dispersions, colloids, or emulsions, as well as sterile powders for reconstitution into sterile injectable solutions, suspensions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

As used herein, "determining" can refer to measuring or ascertaining the presence and severity of an infection, such as, for example, a bacterial infection or a fungal infection that affects a subject's skin, a subject's respiratory system, or affects one or more of a subject's appendages (e.g., at least a portion of one or both feet). Methods and techniques used to determining the presence and/or severity of an infection are typically known to the medical arts. For example, the art is familiar with the ways to identify and/or diagnose the presence, severity, or both of a bacterial infection, a fungal infection, or both.

As used herein, "effective amount" and "amount effective" can refer to an amount that is sufficient to achieve the desired result such as, for example, the treatment and/or prevention of a bacterial infection or a suspected bacterial infection or a fungal infection or a suspected fungal infection. As used herein, the terms "effective amount" and "amount effective" can refer to an amount that is sufficient to achieve the desired an effect on an undesired condition (e.g., a bacterial or a fungal infection). For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific compounded composition employed; the age, body weight, general health, sex and diet of the patient; the time of administration; the route of administration; the rate of excretion of the specific compounded composition employed; the duration of the treatment; drugs used in combination or coincidental with the specific compounded composition employed and like factors well known in the medical arts. For example, it is well within the skill of the art to start doses of a compounded composition at levels lower than those required to achieve the desired therapeutic effect and to gradually increase the dosage until the desired effect is achieved. If desired, then the effective daily dose can be divided into multiple doses for purposes of administration. Consequently, single dose compounded compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition, such as, for example, a bacterial infection or a fungal infection.

Disclosed are the components to be used to prepare a disclosed compounded compositions as well as the disclosed compounded compositions to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

B. Anti-Infective Agents

As used herein, an anti-infective agent can be an antibacterial agent, an antifungal agent, a combination of antibacterial agents, a combination of antifungal agents, or a combination of antibacterial agents and antifungal agents.

Antibacterial agents are known to the art. For example, the art generally recognizes several categories of antibacterial agents including (1) enicillins, (2) cephalosporins, (3) fluoroquinolones, (4) aminoglycosides, (5) monobactams, (6) carbapenems, (7) macrolides, and (8) other agents. For example, as used herein, an antibacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin (piperacillin/tazobactam), pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, streptomycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or pharmaceutically acceptable salts thereof, or a combination thereof. In an aspect, fluoroquinolones can comprise enoxacin, ciprofloxacin, norfloxacin, ofloxacin, levofloxacin, trovafloxacin, gatifloxacin, and moxifloxacin.

Antifungal agents may include (1) azoles (imidazoles), (2) antimetabolites, (3) allylamines, (4) morpholine, (5) glucan synthesis inhibitors (echinocandins), (6) polyenes, (7) benoxaaborale; (8) other antifungal/onychomycosis agents, and (9) new classes of antifungal/onychomycosis agents. For example, as used herein, an antifungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or pharmaceutically acceptable salts thereof, or a combination thereof. In an aspect, azoles can comprise clotrimazole, econazole, oxiconazole, ketoconazole, miconazole, sulconazole, fluconazole, itraconazole, and voriconazole.

In an aspect, an antifungal agent or antibacterial agent can comprise an ointment or can comprise a dry powder. In an aspect, the dry powder can be obtained from crushed tablets comprising an antifungal agent or from a container comprising the antifungal agent as a dry powder. In an aspect, an antifungal agent can be pure or substantially pure and can be obtained from a bulk source. In an aspect, an antifungal agent can be commercially available as, for example, a tablet, a cream, an ointment, or a powder.

As used herein, the recitation of any anti-infective agent inherently encompasses the pharmaceutically acceptable salts thereof.

C. Compounded Compositions

Disclosed herein are compounded compositions for treating an infection.

1. A First Antibacterial Agent and a Second Anti-Infective Agent

Disclosed herein is a compounded composition comprising a therapeutically effective amount of a first antibacterial agent and a therapeutically effective amount of a second antibacterial agent. A disclosed compounded composition can comprise a dry powder formulation or can comprise an ointment.

In an aspect, a disclosed compounded composition can comprise from about 1.0% w/w to about 9.0% w/w, from about 2.0% w/w to about 8.0% w/w, from about 3.0% w/w to about 7.0% w/w, or from about 4.0% w/w to about 7.0% w/w of the first antibacterial agent. In an aspect, a disclosed compounded composition can comprise from about 1.0% w/w to about 9.0% w/w, from about 2.0% w/w to about 8.0% w/w, from about 3.0% w/w to about 7.0% w/w, or from about 4.0% w/w to about 7.0% w/w of the second antibacterial agent.

The first antibacterial agent may include one or more antibacterials or pharmaceutically acceptable salts thereof selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin (piperacillin/tazobactam), pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, streptomycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or pharmaceutically acceptable salts thereof, or a combination thereof. In an aspect, fluoroquinolones can comprise enoxacin, ciprofloxacin, norfloxacin, ofloxacin, levofloxacin, trovafloxacin, gatifloxacin, or moxifloxacin, as discussed supra.

In an aspect, the first antibacterial agent can comprise mupirocin. Disclosed herein is a compounded composition comprising a therapeutically effective amount of mupirocin and a therapeutically effective amount of a second antibacterial agent. In an aspect, a disclosed compounded composition comprising mupirocin and a second antibacterial agent can comprise a dry powder formulation or can comprise an ointment.

In an aspect, a disclosed compounded composition comprising mupirocin and an antibacterial agent can comprise from about 1.0% w/w to about 3.0% w/w mupirocin. In an aspect, a disclosed compounded composition comprising mupirocin and an antibacterial agent can comprise about 1.6% w/w, or about 1.7% w/w, or about 1.8% w/w mupirocin. In an aspect, a disclosed compounded composition comprising mupirocin and an antibacterial agent can comprise from about 1.0% w/w to about 9.0% w/w, from about 2.0% w/w to about 8.0% w/w, from about 3.0% w/w to about 7.0% w/w, from about 4.0% w/w to about 6.0% w/w, or about 5.0% w/w of the antibacterial agent. In an aspect, a disclosed compounded composition comprising mupirocin and an antibacterial agent can comprise about 2.5% w/w, about 5.0% w/w, about 6.0%, or about 7.5% w/w of the antibacterial agent (which is in addition to the amount of mupirocin). Greater or lesser amounts of mupirocin may be used, e.g., less than about 4%, about 3%, about 2%, or about 1% mupirocin.

In an aspect, the first antibacterial agent comprises a therapeutically effective amount of streptomycin. In some embodiments, the compounded composition comprises a therapeutically effective amount of streptomycin and a therapeutically effective amount of a second antibacterial agent. In an aspect, a disclosed compounded composition comprising streptomycin alone or in combination with a second antibacterial agent comprises a dry powder formulation or ointment. As described in more detail below, the dry powder or ointment may be further compounded with a diluent, which may also be a carrier, to formulate a compounded composition comprising a cream, ointment, emulsion (o/w, w/o), gel, jelly, wax, solution. The compounded composition may be formulated for topical administration for local or systemic action. In various embodiments, the compounded composition comprises a topical composition for otic, nasal, upper or lower respiratory tract administration.

The second antibacterial agent may include one or more antibacterials or pharmaceutically acceptable salts thereof selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin (piperacillin/tazobactam), pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, streptomycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or pharmaceutically acceptable salts thereof, or a combination thereof. In an aspect, fluoroquinolones can comprise enoxacin, ciprofloxacin, norfloxacin, ofloxacin, levofloxacin, trovafloxacin, gatifloxacin, or moxifloxacin, as discussed supra.

In an aspect, a disclosed compounded composition comprising streptomycin and a second antibacterial agent comprises from about 1.0% w/w to about 10.0% w/w streptomycin. In an aspect, a disclosed compounded composition comprising streptomycin and a second antibacterial agent comprises about 3% w/w, or about 6% w/w, or about 8% w/w streptomycin. In an aspect, a disclosed compounded composition comprising streptomycin and a second antibacterial agent comprises from about 1.0% w/w to about 9.0% w/w, from about 2.0% w/w to about 8.0% w/w, from about 3.0% w/w to about 7.0% w/w, from about 4.0% w/w to about 6.0% w/w, or about 5.0% w/w of the second antibacterial agent. Greater or lesser amounts of streptomycin or second antibacterial agent may be used, e.g., less than about 1.5%, about 1%, about 0.5%, or about 0.25% second antibacterial agent by weight. In various embodiments, the compounded composition comprising a dry powder, topical solution, or other compounded topical formulation includes an amount of streptomycin configured to provide less than or equal to 1 gm of delivered streptomycin per day, such as less than about 25 mg, about 50 mg, about 75 mg, about 100 mg, about 200 mg, about 300 mg, about 400 mg, about 500 mg, about 600 mg, about 700 mg, about 800 mg, or about 900 mg. For example, the strength of a compounded composition for topical administration with respect to streptomycin may be determined by the amount of streptomycin that may be delivered using the desired format and number of treatments per day. Accordingly, the compounded composition may be formulated such that it may be contacted with a body surface of a subject that is infected or suspected to be infected with a suitable amount of the compounded composition to topically deliver between 25 mg and 1 gm of streptomycin per day, such as between about 25 mg and about 900 mg, about 25 mg and about 500 mg, about 25 mg and about 200 mg, about 50 mg and about 1 gm, about 50 mg and about 800 mg, about 50 mg and about 500 mg, about 50 mg and about 200 mg, about 100 mg and about 1 gm, about 100 mg and about 800 mg, about 100 mg and about 500 mg, about 300 mg and about 1 gm, about 300 mg and about 800 mg, about 300 mg and about 500 mg, about 500 mg and about 1 gm, about 500 mg and about 800 mg, or about 800 mg and about 1 gm. The ratio of second anti-infective agent, when present, to streptomycin in a compounded composition, which may include compounded capsules, compounded ointments, compounded topical compositions obtained by mixing a compounded composition, such as a compounded capsule or compounded ointment, with a diluent at the time of administration, may be about 1:1, about 1:2, about 1:3, about 1:4, about 1:5, about 1:6, about 1:7, about 1:8, about 1:9, about 1:10, about 1:12, about 1:14, about 1:15, about 1:20, or less. In various embodiments, the ratio of the second anti-infective agent to the first anti-infective agent is between about 1:1 and 1:20, 1:2 and about 1:15, about 1:3 and about 1:15, about 1:3 and about 1:10, about 1:4 and about 1:15, or about 1:4 and about 1:10.

In an aspect, the second antibacterial agent can comprise colistimethate. The colistimethate may be compounded from a dry powder such as colistimethate for injection. In an aspect, the second antibacterial agent comprises tobramycin or a pharmaceutically acceptable salt thereof. The tobramycin may be compounded as tobramycin sulfate. In an aspect, the second antibacterial agent can comprise doxycycline or a pharmaceutically acceptable salt thereof. In an aspect, the second antibacterial agent can comprise doxycycline hyclate. In an aspect, the second antibacterial agent can comprise azithromycin. In an aspect, the first antibacterial agent can comprise mupirocin and the second antibacterial agent can comprise one or more of bacitracin, colistimethate, piperacillin-tazobactam, polymyxin B, streptomycin or pharmaceutically acceptable salts thereof. In an aspect, the first antibacterial agent comprises mupirocin and the second antibacterial agent comprises an antibacterial selected from colistimethate, clindamycin, levofloxacin, streptomycin, or combination thereof. In an aspect, the first antibacterial agent comprises streptomycin and the second antibacterial agent comprises an antibacterial selected from colistimethate, clindamycin, levofloxacin, mupirocin, or combination thereof. One or both of the first antibacterial agent or the second antibacterial agent may comprise dry powder for injection. In one example, the streptomycin comprises streptomycin for injection USP. In a further example, the streptomycin comprises streptomycin sulfate for injection USP. In one example, the mupirocin comprises a dry powder, such as a bulk powder. The mupirocin can comprise an ointment (for example, a mupirocin 2.0% ointment) and the second antibacterial agent may comprise a dry powder. In one embodiment, the second antibacterial agent comprises bacitracin. In one example, the bacitracin comprises bacitracin for injection (USP). In another embodiment, the second antibacterial agent comprises colistimethate. In one example, the colistimethate comprises colistimethate for injection. In a further example, the colistimethate includes colistimethate for injection comprising colistimethate sodium or pentasodium colistin methanesulfonate. In another embodiment, the second antibacterial agent comprises piperacillin-tazobactam. In one example, the piperacillin-tazobactam comprises piperacillin-tazobactam for injection USP. In a further example, the piperacillin-tazobactam comprises piperacillin-tazobactam for injection USP selected from 2.25 gram, 3.375 gram, and 4.5 gram vials. In another embodiment, the second antibacterial agent comprises polymyxin B. In one example, the polymyxin B comprises Polymyxin B for Injection USP. In another embodiment, the second antibacterial agent comprises streptomycin.

In various embodiments, the second anti-infective agent comprises an antifungal agent comprising one or more antifungals pharmaceutically acceptable salts thereof selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or pharmaceutically acceptable salts thereof, or a combination thereof. In an aspect, azoles can comprise clotrimazole, econazole, oxiconazole, ketoconazole, miconazole, sulconazole, fluconazole, itraconazole, or voriconazole, as discussed supra. The antifungal agent may be in addition to or instead of the second antibacterial agent.

In one embodiment, a compounded composition comprises a therapeutically effective amount of mupirocin, streptomycin, or both and a therapeutically effective amount of an antifungal agent. A disclosed compounded composition comprising mupirocin, streptomycin, or both and the antifungal agent can comprise a dry powder formulation or can comprise an ointment. As described in more detail elsewhere in the present disclosure, the dry powder or ointment may be further compounded with a carrier or diluent to formulate a compounded composition comprising a cream, ointment, emulsion (o/w, w/o), gel, jelly, wax, solution. The compounded composition may be formulated for topical administration for local or systemic action. In various embodiments, the compounded composition comprises a topical composition for otic, nasal, upper or lower respiratory tract administration.

The antifungal agent may comprise one or more antifungals selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or pharmaceutically acceptable salts thereof, or a combination thereof. In an aspect, azoles can comprise clotrimazole, econazole, oxiconazole, ketoconazole, miconazole, sulconazole, fluconazole, itraconazole, or voriconazole, as discussed supra. The antifungal agent may be in addition to or instead of the second antibacterial agent.

In an aspect, a disclosed compounded composition comprising streptomycin and an antifungal agent comprises from about 1.0% w/w to about 10.0% w/w streptomycin. In an aspect, a disclosed compounded composition comprising streptomycin and an antifungal agent comprises about 3% w/w, or about 6% w/w, or about 8% w/w streptomycin. In an aspect, a disclosed compounded composition comprising streptomycin and an antifungal agent comprises from about 1.0% w/w to about 9.0% w/w, from about 2.0% w/w to about 8.0% w/w, from about 3.0% w/w to about 7.0% w/w, from about 4.0% w/w to about 6.0% w/w, or about 5.0% w/w of the antifungal agent. Greater or lesser amounts of streptomycin or second antibacterial agent may be used, e.g., less than about 1.5%, about 1%, about 0.5%, or about 0.25% antifungal agent by weight.

In an aspect, a disclosed compounded composition can comprise a therapeutically effective amount of one or more additional anti-infective agents. In an aspect, the additional anti-infective agent can be an antibacterial agent. Antibacterial agents are known to the art and discussed supra. In an aspect, the additional anti-infective agent can be an antifungal agent. In an aspect, the antifungal agent can comprise ketoconazole.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

Disclosed herein is a compounded composition comprising a therapeutically effective amount of an anti-infective comprising at least streptomycin. The streptomycin may comprise a dry powder, such as a powder for injection.

The compounded composition may include multiple anti-infectives in combination with streptomycin, such as streptomycin for injection. The multiple anti-infectives may be selected from any combination of the antibacterial and antifungals described herein. In one example, one or more of the anti-infectives may comprise one or more antibacterials or pharmaceutically acceptable salt thereof selected from bacitracin, colistimethate, piperacillin-tazobactam, polymyxin B, streptomycin, or combination thereof and/or one or more one or more antifungals or pharmaceutically acceptable salt thereof selected from voriconazole, amphotericin B, or combination thereof. In these or other embodiments, one or more of the anti-infectives may comprise the antibacterial doxycycline or pharmaceutically acceptable salt and/or the antifungal ketoconazole or pharmaceutically acceptable salt thereof. In some embodiments, streptomycin alone or in combination with one or more additional anti-infectives may be compounded in an ointment. In various embodiments, the compounded composition comprising a compounded ointment may include about 20% or less streptomycin by weight. In some examples, the compounded ointment may include from about 1% to about 15%, about 1% to about 10%, about 1% to about 5%, about 5% to about 10% streptomycin by weight.

In various embodiments, the compounded composition comprises a dry powder formulation, ointment, or combination thereof comprising streptomycin alone or in combination with another anti-infective as described herein and may be formulated for direct administration or mixing with a diluent, which may also be or comprise a carrier. For example, a dry powder formulation may be utilized as an inhalable powder or wound powder, which may be administered directly. In some embodiments, the diluent may comprise a liquid, e.g., an aqueous or organic diluent, a dry powder diluent, a topical cream, lotion, ointment, emulsion (o/w, w/o), gel, wax, or jelly. For example, a dry powder formulation may be mixed with a diluent comprising a dry powder diluent wherein the resulting mixture may be administered as an inhalable powder or wound powder. In various embodiments, a dry powder formulation may be formulated to be mixed with a diluent at the time of administration to produce a mixture comprising the compounded composition having about 20% or less streptomycin by weight. In some examples, the mixture comprising the compounded composition may include from about 1% to about 15%, about 1% to about 10%, about 1% to about 5%, about 5% to about 10% streptomycin by weight.

In one example, the compounded composition a dry powder formulation or compounded ointment is formulated for mixing with a liquid diluent just prior to administration. In various embodiments, for example, a resulting mixture comprises a topical composition for irrigation, e.g., wound irrigation to treat broken tissue or administration to infected skin in a foot bath. In some embodiments, the resulting mixture comprises a topical solution for nasal administration or administration to the upper or lower respiratory tract, e.g., in a nasal spray, mist, drop, irrigation, nebulization formulation. In some embodiments, the resulting mixture comprises a topical solution for otic administration or administration to the upper or lower respiratory tract, e.g., in a nasal spray, mist, drop, irrigation, or nebulization formulation.

In another example, the compounded composition is formulated for mixing with a dry powder diluent such as lactose for administration by inhalation. In another example, the compounded composition is formulated for mixing with a dry powder diluent for administration to a wound comprising broken tissue, such as a wet wound whereby the resulting dry powder mixture contacts the wet wound and at least partially solubilizes thereon.

In another example, the compounded composition is formulated for mixing with a topical cream, lotion, ointment, gel, emulsion (o/w, w/o), wax, or jelly. The resulting mixture may be applied to skin or other body surface for topical administration. In one example, the resulting mixture may be applied to a medical instrument for application to skin or a body surface, such as a body orifice, or for providing a barrier between the instrument and the skin or body surface during a procedure. In one example, the compounded composition comprises a dry powder of one or more antibacterial agents formulated to be mixed with an anti-infective comprising an ointment such as a commercially available mupirocin ointment.

In some embodiments, a compounded composition may include a compounded ointment comprising streptomycin. The compounded ointment may be compounded from a dry powder streptomycin, e.g., streptomycin for injection such as streptomycin sulfate for injection. The compounded composition comprising a compounded ointment may include about 20% or less streptomycin by weight. In some examples, the compounded ointment may include from about 1% to about 15%, about 1% to about 10%, about 1% to about 5%, about 5% to about 10% streptomycin by weight. In various embodiments, the compounded ointment may include between about 1% and about 10% streptomycin by weight. The compounded ointment may be further compounded with the second antibacterial agent comprising a dry powder or ointment, which may be applied directly to infected skin or may be further combined with an aqueous diluent for irrigation administration, e.g., in a foot bath. In some embodiments, the dry powder formulation comprising streptomycin alone or in combination with one or more second anti-infectives may be applied directly to infected skin. For example, a dry powder formulation comprising streptomycin alone or in combination with one or more additional anti-infectives may be applied to infected and/or broken tissues, such as a wet wound. In some embodiments, the dry powder formulation comprising streptomycin alone or in combination with one or more second anti-infectives may be mixed with a suitable diluent as described above and elsewhere herein. In one embodiment, a dry powder formulation comprising streptomycin alone or in combination with one or more additional anti-infectives may be compounded with an ointment comprising an additional anti-infective. For example, a dry powder formulation comprising streptomycin alone or in combination with one or more additional anti-infectives may be mixed with a mupirocin ointment to form a compounded ointment. In an aspect a disclosed composition comprises an ointment comprising a therapeutic amount of streptomycin. In one example, the ointment comprises streptomycin in an amount between about 1% and about 10% by weight. In a further embodiment, the ointment may comprise an additional anti-infective such as one or more antibacterial or antifungal agents as described herein. For example, the second anti-infective may comprise an antibacterial selected from colistimethate, clindamycin, mupirocin, levofloxacin, or combination thereof.

As introduced above, the compounded composition may include additional anti-infectives, such as a second antibacterial agent and an antifungal agent may comprise powders. In an aspect, the compounded composition may include an amount of second antibacterial agent from about 1% to about 30%, about 1% to about 20%, about 1% to about 10%, about 1% to about 5%, about 4% to about 15%, about 4% to about 10%, or about 4% to about 8% w/w. In an aspect, the compounded composition may include an amount of antifungal agent from about 1% to about 30%, about 1% to about 20%, about 1% to about 10%, about 1% to about 5%, about 2% to about 15%, about 2% to about 10%, or about 2% to about 8% w/w. In various embodiments, the powders may comprise anti-infective tablets (ground, e.g., crushed), bulk powder, or anti-infective for injection. Anti-infectives for injection may comprise powder, typically available in vials, for reconstitution.

In some embodiments, the compounded composition may include from about 1% to about 30%, about 1% to about 20%, about 4% to about 20%, about 4% to about 15% w/w anti-infective for injection. In various embodiments, the compounded composition comprises anti-infective for injection in an amount between about 3% and about 20% w/w. In an aspect, the anti-infective for injection comprises streptomycin sulfate for injection. In an aspect, the anti-infectective for injection comprises streptomycin sulfate for injection and one or more of bacitracin for injection, colistimethate sodium for injection, pentasodium colistin methanesulfonate for injection, piperacillin-tazobactam for injection, polymyxin B for injection USP, tobramycin sulfate for injection, voriconazole for injection, or amphotericin B for injection. In these or other embodiments, the compounded composition may include from about 1% to about 30%, about 1% to about 20%, about 1% to about 10%, about 3% to about 15%, or about 4% to about 12% crushed anti-infective tablets.

In various embodiments, the compounded composition comprises a sufficient amount of an excipient base powder comprising a blend of micronized xylitol and poloxamers, and a sufficient amount of xylitol. In an aspect, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. Excipient base powders are known to the art and discussed supra. In an aspect, a disclosed compounded composition comprising an excipient base powder and xylitol can comprise a weight ratio of excipient base powder to xylitol of about 1:1, about 1:2, about 1:3, about 1:4, about 1:5, about 1:6, about 1:7, from about 1:1 to about 1:7, from about 1:2 to about 1:6, or from about 1:4 to about 1:5. In an aspect, the weight ratio of excipient base powder to xylitol can be about 1:4.35.

2. Capsules

In various embodiments, a container may be provided to contain the compounded composition. For example, the compounded composition may be contained in one or more capsules. Capsules may include dry powder obtained from crushed tablets, bulk powders, antimicrobials for injection, or combinations thereof.

In an aspect, a disclosed capsule can comprise about 100 mg to about 2000 mg of a disclosed compounded composition. In an aspect, a disclosed capsule can comprise about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg of a disclosed compounded composition.

In an aspect, a disclosed capsule comprising a disclosed compounded composition can be broken apart such that its contents can be retrieved. In an aspect, a disclosed capsule can be dissolved in water such that its contents can be contacted with the water.

In an aspect, a disclosed capsule can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra.

In one embodiment, a compounded capsule comprises between about 25 mg and about 500 mg streptomycin with streptomycin being the primary ingredient in the capsule. In some embodiments, the compounded capsule includes a second anti-infective comprising one or more anti-infectives, such as antibacterials and/or antifungals described herein. For example, the second anti-infective may comprise an antibacterial selected from colistimethate, clindamycin, mupirocin, levofloxacin, or combination thereof.

In an aspect, a compounded capsule may include between about 50 mg and about 250 mg streptomycin. In some embodiments, the compounded capsule may include a second anti-infective agent comprising one or more additional anti-infectives comprising an antibacterial, antifungal, or combination thereof. The second anti-infective may be present in an amount less than or greater than the streptomycin. In various embodiments, the second anti-infective agent may be present in lesser amount than the streptomycin. For example, the second anti-infective agent may be present in an amount less than about 100 mg, less than about 75 mg, less than about 50 mg, or less than about 25 mg. In various embodiments, a compounded capsule may include a second anti-infective agent comprising an antibacterial selected from colistimethate, clindamycin, mupirocin, levofloxacin, or combination thereof. In some embodiments, the second anti-infective agent may be present in an amount between about 25 mg and about 100 mg, about 25 mg and about 25 mg, about 25 mg and about 50 mg, or about 50 mg and about 75 mg. For example, in one embodiment, a compounded capsule includes between about 50 mg and about 225 mg streptomycin and between about 25 and about 75 mg colistimethate. In another example, a compounded capsule includes between about 50 mg and about 225 mg streptomycin and between about 25 mg and about 50 mg mupirocin.

In various embodiments, the anti-infectives may be obtained from bulk powder, crushed tablets, or injectable powders as described herein. In an aspect, a disclosed capsule or the contents thereof may be combined with a carrier or diluent to formulate a compounded composition comprising a powder, cream, ointment, emulsion (o/w, w/o), gel, jelly, wax, solution. A compounded ointment, for example, may include an antibacterial agent comprising between about 1% and about 10% streptomycin by weight. The compounded ointment may also include one or more additional anti-infectives. The additional anti-infective, when included, may be present in an amount less than or greater than the streptomycin, such as less or greater than about 10%, less than about 5%, less than about 3%, less than about 1% by weight.

In an aspect, a disclosed capsule can comprise one or more excipients or additives. In an aspect, excipients or additives include, but are not limited to, the following: solvents, surfactants, humectants, preservatives, flavorings, stabilizers (including antioxidants), binders, and colorants.

3. Kits

Disclosed herein is a kit, comprising: a plurality of containers, each container comprising a compounded composition.

In an aspect, the plurality of containers can comprise more than 1 container. In an aspect, the plurality can comprise at least 3 containers, at least 7 containers, or at least 10 containers, at least 14 containers, at least 21 containers, at least 30 containers, at least 60 containers, at least 90 containers, at least 120 containers, or at least 150 containers, or more than 150 containers.

In an aspect, the plurality of containers can comprise a 3 day's supply, or a week's supply, or a 10 day's supply, or a two week's supply, or a month's supply, or a two month's supply, or a three month's supply, or a six month's supply, or more than a six month's supply of a disclosed compounded composition.

It will be apprechiated that the compouned composition may be provided in containers other than a capsule. For example, the compounded composition may be provided in a pouch, vial, or other suitable container. For example, a kit may comprise one or more capsules containing a therapeutically effective of amount of one or more anti-infectives as described herein, such as mupirocin or streptomycin, in a dry powder formulation or ointment, and a diluent, which may comprise a carrier. The diluent may comprise a dry powder, cream, ointment, emulsion (o/w, w/o), gel, jelly, wax, solution. Solutions may include, for example, water (e.g., potable water, sterile water, water for injection), aqueous based solutions, oil based solutions, organic solvents, saline (e.g., 0.9% saline, normal saline), povidone iodine, sodium hypochlorite (Dakin's solution), hydrogen peroxide, cleansers (e.g., wound cleansers). Such solutions may be sterile solutions. Prior to, e.g., at the time of administration, of the compounded composition, the contents of the capsule may be mixed with the carrier or diluent.

In some embodiments, a kit comprising the compounded composition is provided compounded in the diluent. For example, the compounded composition may comprise a cream, ointment, emulsion (o/w, w/o), gel, jelly, wax, solution comprising one or more anti-infectives as described herein. In one example, a kit comprises a compounded composition in the form of a compounded ointment and that may be further mixed with a diluent prior to administration, e.g., for administration in a foot bath, irrigation format, or otherwise. In various embodiments, a kit includes a compounded composition comprising a dry powder. The dry powder may be provided in one or more containers, e.g., one or more compounded capsules. For example, a kit may include a compounded capsule comprising between about 50 mg and about 250 mg streptomycin. In some embodiments, the compounded capsule may include a second anti-infective agent comprising one or more additional anti-infectives comprising an antibacterial, antifungal, or combination thereof. The second anti-infective may be present in an amount less than or greater than the streptomycin. In various embodiments, the second anti-infective agent may be present in lesser amount than the streptomycin. For example, the second anti-infective agent may be present in an amount less than about 100 mg, less than about 75 mg, less than about 50 mg, or less than about 25 mg. In various embodiments, a compounded capsule may include a second anti-infective agent comprising an antibacterial selected from colistimethate, clindamycin, mupirocin, levofloxacin, or combination thereof. In some embodiments, the second anti-infective agent may be present in an amount between about 25 mg and about 100 mg, about 25 mg and about 25 mg, about 25 mg and about 50 mg, or about 50 mg and about 75 mg. For example, in one embodiment, a compounded capsule includes between about 50 mg and about 225 mg streptomycin and between about 25 and about 75 mg colistimethate. In another example, a compounded capsule includes between about 50 mg and about 225 mg streptomycin and between about 25 mg and about 50 mg mupirocin.

In various embodiments, a kit includes one or more anti-infectives comprising streptomycin alone or in combination with one or more anti-infectives as described herein. The streptomycin may be provided as a dry powder, which may be contained in a container such as a capsule alone or in combination with one or more additional anti-infectives as described herein. In one embodiment, the additional anti-infective comprises one or more anti-infectives selected from colistimethate, clindamycin, mupirocin, levofloxacin, or combination thereof. One or more additional anti-infectives may be provided in the kit in another format, e.g., a solution, ointment, or other suitable format. For example, a kit may comprise streptomycin powder and mupirocin ointment, such as mupirocin 2% ointment. The streptomycin powder may be mixed with the mupirocin ointment prior to administration. The kit may also include diluents to be mixed with the combination powder and ointment.

In various embodiments, a kit comprising a dry powder formulation of streptomycin alone or in combination with one or more additional anti-infectives may comprise an inhalable powder or wound powder formulation configured to be administered directly to a subject's tissues. In one embodiment, the additional anti-infective one or more antibacterials selected from colistimethate, clindamycin, mupirocin, levofloxacin, or combination thereof. In one example, the kit may provide a nebulization formulation whereby, at the time of administration, the dry powder formulation may be mixed with a suitable sterile liquid diluent for nebulization.

In an embodiment, a kit comprises a compounded ointment comprising streptomycin alone or in combination with one or more additional anti-infectives, such as an antibacterial agent and/or an antifungal agent. In one example, a kit comprises a compounded ointment comprising streptomycin in combination with one or more antibacterials selected from colistimethate, clindamycin, mupirocin, levofloxacin, or combination thereof. In some embodiments, the compounded ointment includes from about 1% to about 15%, about 1% to about 10%, about 1% to about 5%, about 5% to about 10% streptomycin by weight.

In various embodiments, a kit comprising a compounded ointment comprising streptomycin alone or in combination with one or more additional anti-infectives as described herein may also include a diluent for mixing with the anti-infectives prior to or at the time of administration. In one example, one or more additional anti-infectives may comprise colistimethate, clindamycin, mupirocin, levofloxacin, or combination thereof. The diluent may comprise a dry powder, cream, ointment, emulsion (o/w, w/o), gel, jelly, wax, solution. Solutions may include, for example, water (e.g., potable water, sterile water, water for injection), aqueous based solutions, oil based solutions, organic solvents, saline (e.g., 0.9% saline, normal saline), povidone iodine, sodium hypochlorite (Dakin's solution), hydrogen peroxide, cleansers (e.g., wound cleansers). Prior to, e.g., at the time of administration, of the compounded composition, a suitable amount of the compounded ointment may be mixed with the carrier or diluent.

As noted above, a kit comprising a dry powder formulation or ointment including an anti-infective agent such as streptomycin alone or in combination with one or more additional anti-infective agents may comprise a diluent for mixing with the dry powder formulation at the time of administration. In various embodiments, a dry powder formulation may be formulated to be mixed with a diluent at the time of administration to produce a mixture comprising the compounded composition having about 20% or less streptomycin by weight. In some examples, the mixture comprising the compounded composition may include from about 1% to about 15%, about 1% to about 10%, about 1% to about 5%, about 5% to about 10% streptomycin by weight. In various embodiments, the diluent may comprise a liquid, e.g., an aqueous or organic diluent, a dry powder diluent, a topical cream, lotion, ointment, emulsion (o/w, w/o), gel, wax, or jelly. For example, a dry powder formulation may be mixed with a diluent comprising a dry powder diluent wherein the resulting mixture may be administered as an inhalable powder or wound powder. In one example, the kit comprising the compounded composition includes a liquid diluent for mixing with the compound composition at the time of administration. The liquid diluent may comprise a sterile liquid. In various embodiments, for example, a resulting mixture comprises a topical composition for irrigation, e.g., wound irrigation for broken tissue or administration to infected skin in a foot bath. In some embodiments, the resulting mixture comprises a topical solution for nasal administration or administration to the upper or lower respiratory tract, e.g., in a nasal spray, mist, drop, irrigation, nebulization formulation. In some embodiments, the resulting mixture comprises a topical solution for otic administration.

In another example, a kit comprises a compounded composition comprising streptomycin alone or in combination with an additional anti-infective and a dry powder diluent for mixing prior to administration. For example, the dry powder diluent may comprise lactose whereby the resulting mixture is formulated for administration by inhalation. In another example, a kit comprises a compounded composition comprising streptomycin alone or in combination with an additional anti-infective and a dry powder diluent configured for mixing prior to administration to a wound and/or broken tissue, such as a wet wound, whereby the resulting dry powder mixture contacts the wet wound and at least partially solubilizes thereon. In another example, a kit comprises a compounded composition and a diluent comprising a topical cream, lotion, ointment, gel, emulsion (o/w, w/o), wax, or jelly for mixing prior to administration. The resulting mixture may be applied to skin or other body surface for topical administration. In one example, the resulting mixture may be applied to a medical instrument for application to skin or a body surface, such as a body orifice, or for providing a barrier between the instrument and the skin or body surface during a procedure. In one example, the compounded composition comprises a dry powder of one or more antibacterial agents formulated to be mixed with an anti-infective comprising an ointment such as a commercially available mupirocin ointment.

In various embodiments, the compounded composition comprising a dry powder, topical solution, or other compounded topical formulation includes an amount of streptomycin configured to provide less than or equal to 1 gm of delivered streptomycin per day, such as less than about 25 mg, about 50 mg, about 75 mg, about 100 mg, about 200 mg, about 300 mg, about 400 mg, about 500 mg, about 600 mg, about 700 mg, about 800 mg, or about 900 mg. For example, the strength of a compounded composition for topical administration with respect to streptomycin may be determined by the amount of streptomycin that may be delivered using the desired format and number of treatments per day. Accordingly, a kit may include a suitable amount of diluent to formulate the mixed compounded composition for administration. Thus, according to at least one embodiment, the compounded composition may be formulated such that it may be contacted with a body surface of a subject that is infected or suspected to be infected with a suitable amount of the compounded composition to topically deliver between 25 mg and 1 gm of streptomycin per day, such as between about 25 mg and about 900 mg, about 25 mg and about 500 mg, about 25 mg and about 200 mg, about 50 mg and about 1 gm, about 50 mg and about 800 mg, about 50 mg and about 500 mg, about 50 mg and about 200 mg, about 100 mg and about 1 gm, about 100 mg and about 800 mg, about 100 mg and about 500 mg, about 300 mg and about 1 gm, about 300 mg and about 800 mg, about 300 mg and about 500 mg. about 500 mg and about 1 gm, about 500 mg and about 800 mg, or about 800 mg and about 1 gm. The ratio of second anti-infective agent, when present, to streptomycin in a compounded composition, which may include compounded capsules, compounded ointments, compounded topical compositions obtained by mixing a compounded composition, such as a compounded capsule or compounded ointment, with a diluent at the time of administration, may be about 1:1, about 1:2, about 1:3, about 1:4, about 1:5, about 1:6, about 1:7, about 1:8, about 1:9, about 1:10, about 1:12, about 1:14, about 1:15, about 1:20, or less. In various embodiments, the ratio of the second anti-infective agent to the first anti-infective agent is between about 1:1 and 1:20, 1:2 and about 1:15, about 1:3 and about 1:15, about 1:3 and about 1:10, about 1:4 and about 1:15, or about 1:4 and about 1:10. In an aspect, a disclosed kit can comprise a foot bath. Foot baths are known to the art and are discussed supra. In an aspect, a disclosed kit can comprise one or more funnels. In an aspect, a disclosed kit can comprise one or more mixing containers. In an aspect, a disclosed kit can comprise one or more scoops or spoons, such as a 5 cc scoop or spoon or a 1 cc scoop or spoon. In an aspect, a disclosed kit can comprise one or more keys. In an aspect, a disclosed kit can comprise a diluent for a disclosed compounded composition. In an aspect, a diluent can comprise sodium hypochlorite. In an aspect, a diluent can comprise Dakin's solution. In an aspect, a disclosed kit can comprise one or more bottles of diluent.

In an aspect, a disclosed kit can comprise non-stick, hypo-allergenic tape, sterile pads, sterile applicators (e.g., sterile 6 inch applicators), or a combination thereof. In an aspect, a disclosed kit can comprise one or more bottles of a cleaning solution or suspension, such as a liquid skin cleanser. In an aspect, the cleaning solution or suspension can be Hibiclens.

In an aspect, the disclosed kit comprises a foot bath starter pack. The foot bath starter pack may be suitable for administering one or more of the compounded compositions described herein, e.g., foot bath compositions and foot bath solutions. In various aspects, the foot bath starter pack includes a foot bath, 1 to 2 bottle(s) of diluent, a funnel, a mixing container, and a measuring device for measuring powder medications, e.g., one or two spoons/scoops, such as those described above.

In one aspect, the compounded composition includes a compounded powder comprising about 25% (w/w) mupirocin and about 25% (w/w) itraconazole. The second anti-infective may be an anti-bacterial agent as described herein. The compounded powder may also include Loxasperse®-Xylifos™ Combination Powder, which may make up the remaining 50% of the compounded powder. A method of treating or preventing an infection, such as a foot infection, with such a composition using the foot bath starter pack may comprise filling the foot bath with warm water to a fill line indicated on the inside of the foot bath. Using the funnel, adding 2 scoops of medication using a first spoon into the mixing container. For every tablespoon of powder, 15 ml of diluent may be added to the mixing container holding the powder. The mixture may then be mixed, e.g., by shaking or stirring. The foot bath may then be turned on and the water therein allowed to agitate. The solution/suspension mixture may then be added to the water. The subject's foot or portion thereof may be placed in the foot bath for a suitable amount of time, such as 10 minutes, or other duration, such as described elsewhere herein. The foot bath starter pack may be configured for use in administration of different compounded compositions and foot bath compositions. For example, in one aspect, a foot bath composition comprises mupirocin or streptomycin and a second anti-infective such as itraconazole or colistimethate. The foot bath compositions may comprises various rations of mupirocin or streptomycin to the second anti-infective, e.g., between about 1:9 and about 9:1, about 1:1, about 1:2, about 1:3, about 2:1, or about 3:1. A method of treating or preventing an infection, such as a foot infection, with such a composition using the foot bath starter pack may comprise filling the foot bath with warm water to a fill line indicated on the inside of the foot bath. Using the funnel, adding 2 scoops of mupirocin or streptomycin, e.g., streptomycin sulfate for injection, powder using a second spoon, different from the first, and one scoop of the second anti-infective using the second spoon, may be added into the mixing container. For every tablespoon of powder, 15 ml of diluent may be added to the mixing container holding the powder. The mixture may then be mixed, e.g., by shaking or stirring. The foot bath may then be turned on and the water therein allowed to agitate. The solution/suspension mixture may then be added to the water. The subject's foot or portion thereof may be placed in the foot bath for a suitable amount of time, such as 10 minutes, or other duration, such as described elsewhere herein.

In a further aspect, the foot bath composition includes a combination ointment and powder. For example, in one aspect, the foot bath composition comprises mupirocin 2% ointment, streptomycin powder, or a compounded streptomycin ointment comprising about 1% to about 10% streptomycin by weight and an antifungal agent, as disclosed herein. The antifungal agent may comprise, for example, one or more of ketoconazole, voriconazole, amphotericin, or nystatin. The antifungal agent may be a dry powder comprising crushed oral tablets, bulk powder, antifungal for injection, or combinations thereof. In one example, the antifungal agent includes nystatin topical powder. A method of treating or preventing an infection, such as a foot infection, with such a composition using the foot bath starter pack may comprise filling the foot bath with warm water to a fill line indicated on the inside of the foot bath. The method may further include opening one bottle of nystatin 15 mg and placing the opening of the bottle into the neck of the mixing container and squeezing until all the powder is removed from the bottle. The method may further include opening a tube of mupironcin 2% ointment or compounded streptomycin ointment comprising about 1% to about 10% streptomycin by weight and emptying at least a portion of the contents of the tube into the mixing container. The compounded streptomycin ointment may comprise one or more additional anti-infectives as described herein or in instances wherein one or more additional anti-infectives are to be compounded to formulate the foot bath solution, additional anti-infectives may be mixed with the ointment, added to the mixing container, added to the solution/suspension mixture, or added to water or mixed streptomycin ointment and water in the foot bath. For every tablespoon of the foot bath composition, 15 ml of diluent may be added to the mixing container holding the composition. The mixture may then be mixed, e.g., by shaking or stirring. The foot bath may then be turned on and the water therein allowed to agitate. The solution/suspension mixture may then be added to the water. The subject's foot or portion thereof may be placed in the foot bath for a suitable amount of time, such as 10 minutes, or other duration, such as described elsewhere herein.

D. Methods of Making a Compounded Composition

Disclosed herein is a method of making a compounded composition, the method comprising: mixing a therapeutically effective amount of a first anti-infective agent, such as first antibacterial agent, and a therapeutically effective amount of a second anti-infective agent, such as one or more antibacterial agents, one or more anti-funcal agents, or combination thereof agent to make a homogenous compounded composition. A disclosed compounded composition can comprise a dry powder formulation or can comprise an ointment.

In an aspect, the mixing can comprise using an electronic mortar and pestle (EMP). In an aspect, a disclosed method can comprise milling the ingredients (using, for example, a three-roll mill). Mixing and milling can be done according to standards known to the skilled person in the art.

In an aspect, a disclosed method can comprise obtaining the first antibacterial agent, obtaining the second antibacterial agent, or a combination thereof. In an aspect, obtaining can comprise obtaining a bulk source of the first antibacterial agent, obtaining a bulk source of the second antibacterial agent, or a combination thereof. In an aspect, a disclosed method can comprise obtaining the antibacterial agent, obtaining the antifungal agent, or a combination thereof. In an aspect, obtaining can comprise obtaining a bulk source of one or more antibacterials of the antibacterial agent or obtaining a bulk source of one or more antifungals of the antifungal agent. In an aspect, a disclosed method can comprise obtaining the first antibacterial agent, obtaining the second antibacterial agent, obtaining the antifungal agent, or a combination thereof. In an aspect, obtaining can comprise obtaining a bulk source of the first antibacterial agent, obtaining a bulk source of the second antibacterial agent, obtaining a bulk source of the antifungal agent, or a combination thereof.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise mixing a compounded ointment or dry powder comprising streptomycin alone or in combination with one or more additional anti-infectives as described herein with a diluent. Mixing may be prior to administration, e.g., at the time of administration. In one example, one or more additional anti-infectives may comprise colistimethate, clindamycin, mupirocin, levofloxacin, or combination thereof. The diluent may comprise a dry powder, cream, ointment, emulsion (o/w, w/o), gel, jelly, wax, solution. Solutions may include, for example, water (e.g., potable water, sterile water, water for injection), aqueous based solutions, oil based solutions, organic solvents, saline (e.g., 0.9% saline, normal saline), povidone iodine, sodium hypochlorite (Dakin's solution), hydrogen peroxide, cleansers (e.g., wound cleansers). The resulting mixure for administration may comprise between about 1% and about 20% streptomycin. When a second or additional anti-infective is present, the resulting mixture for administration may include between about 1% and about 20% second anti-infective by weight.

In various embodiments, a method of making a compounded composition comprising a dry powder, topical solution, or other compounded topical formulation includes formulating the composition to include an amount of streptomycin configured to provide less than or equal to 1 gm of delivered streptomycin per day, such as less than about 25 mg, about 50 mg, about 75 mg, about 100 mg, about 200 mg, about 300 mg, about 400 mg, about 500 mg, about 600 mg, about 700 mg, about 800 mg, or about 900 mg. For example, the strength of a compounded composition for topical administration with respect to streptomycin may be determined by the amount of streptomycin that may be delivered using the desired format and number of treatments per day. Accordingly, a method of making the compounded composition may include combining a suitable amount of diluent to formulate the compounded composition for administration. Thus, according to at least one embodiment, the compounded composition may be formulated such that it may be contacted with a body surface of a subject that is infected or suspected to be infected with a suitable amount of the compounded composition to topically deliver between 25 mg and 1 gm of streptomycin per day, such as between about 25 mg and about 900 mg, about 25 mg and about 500 mg, about 25 mg and about 200 mg, about 50 mg and about 1 gm, about 50 mg and about 800 mg, about 50 mg and about 500 mg, about 50 mg and about 200 mg, about 100 mg and about 1 gm, about 100 mg and about 800 mg, about 100 mg and about 500 mg, about 300 mg and about 1 gm, about 300 mg and about 800 mg, about 300 mg and about 500 mg. about 500 mg and about 1 gm, about 500 mg and about 800 mg, or about 800 mg and about 1 gm. Accordingly, streptomycin and one or more additional anti-infectives, when present, may be compounded with or mixed with a suitable amount of diluent to formulate the compounded composition for administration. The ratio of second anti-infective agent, when present, to streptomycin in a compounded composition, which may include compounded capsules, compounded ointments, compounded topical compositions obtained by mixing a compounded composition, such as a compounded capsule or compounded ointment, with a diluent at the time of administration, may be about 1:1, about 1:2, about 1:3, about 1:4, about 1:5, about 1:6, about 1:7, about 1:8, about 1:9, about 1:10, about 1:12, about 1:14, about 1:15, about 1:20, or less. In various embodiments, the ratio of the second anti-infective agent to the first anti-infective agent is between about 1:1 and 1:20, 1:2 and about 1:15, about 1:3 and about 1:15, about 1:3 and about 1:10, about 1:4 and about 1:15, or about 1:4 and about 1:10.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In various embodiments, a method of making a compounded composition comprises forming a compounded capsule comprising a dry powder. In one embodiment, the compounded capsule may include about 50 mg and about 250 mg streptomycin. In further embodiments, the method may include forming a compounded capsule including a second anti-infective agent comprising one or more additional anti-infectives selected from an antibacterial, antifungal, or combination thereof. The second anti-infective may be present in an amount less than or greater than the streptomycin. In various embodiments, the second anti-infective agent may be present in lesser amount than the streptomycin. For example, the second anti-infective agent may be present in an amount less than about 100 mg, less than about 75 mg, less than about 50 mg, or less than about 25 mg. In various embodiments, the method may include forming a compounded capsule including a second anti-infective agent comprising an antibacterial selected from colistimethate, clindamycin, mupirocin, levofloxacin, or combination thereof. In some embodiments, the method may include combining between about 25 mg and about 100 mg, about 25 mg and about 25 mg, about 25 mg and about 50 mg, or about 50 mg and about 75 mg of the second anti-infective with the streptomycin. For example, in one embodiment, a compounded capsule includes between about 50 mg and about 225 mg streptomycin and between about 25 and about 75 mg colistimethate. In another example, a compounded capsule includes between about 50 mg and about 225 mg streptomycin and between about 25 mg and about 50 mg mupirocin. In one embodiment, a method of making a compounded capsule comprises combining streptomycin sulfate for injection with a base, such as PCCA Loxasperse. In one example, a compounded capsule comprising 225 mg of streptomycin may be formulated by combining 310.95 mg of streptomycin sulfate for injection with 5 mg of PCCA Loxasperse. The streptomycin sulfate for injection may be obtained from 1 g streptomycin vials of streptomycin sulfate for injection, which contained about 1.382 gm streptomycin sulfate. The method may further include combining a second anti-infective in an amount less than about 100 mg, less than about 75 mg, less than about 50 mg, or less than about 25 mg. Depending on the size of the capsule, the amount of streptomycin may be reduced by an amount equivalent to the amount of second anti-infective. In various embodiments, the method may include combining between about 25 mg and about 100 mg, about 25 mg and about 25 mg, about 25 mg and about 50 mg, or about 50 mg and about 75 mg of the second anti-infective with the streptomycin wherein the second anti-infective agent comprises an antibacterial selected from colistimethate, clindamycin, mupirocin, levofloxacin, or combination thereof. In one embodiment, the method includes combining between about 50 mg and about 225 mg streptomycin (or an equivalent amount of streptomycin sulfate for injection) and between about 25 and about 75 mg colistimethate. In another example, the method includes combining between about 50 mg and about 225 mg streptomycin (or an equivalent amount of streptomycin sulfate for injection) and between about 25 mg and about 50 mg mupirocin. The second anti-infectives may comprise a dry powder obtained from bulk powder, crushed tablets, or powder for injection.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition into a container and sealing the container. In an aspect, a container can be a container disclosed herein, such as, for example, a plastic tube, a glass or non-glass vial, a syringe, etc. In an aspect, a disclosed method can comprise sterilizing the compounded composition.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise packaging the compounded composition comprising a first antibacterial agent, a second antibacterial agent, and an antifungal agent into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising a first antibacterial agent, a second antibacterial agent, and an antifungal agent.

E. Methods of Treating or Preventing an Infection Using a Compounded Composition Disclosed herein is a method of treating or preventing an infection, the method comprising: applying to the skin of a subject a compounded composition, wherein the compounded composition comprises any compounded composition disclosed herein.

Disclosed herein is a method of treating or preventing an infection, the method comprising: preparing a homogenous compounded composition comprising any compounded composition disclosed herein.

In an aspect, a disclosed method can comprise orally administering to the subject a pharmaceutical composition comprising one or more additional anti-infective agents. In an aspect, the additional anti-infective agent can be an antibacterial agent, such as any suitable antibacterial agent, e.g., any suitable antibacterial listed herein. In an aspect, the additional anti-infective agent can be an antifungal agent, such as any suitable antifungal agent, e.g., any suitable antifungal agent listed herein.

In an aspect, a disclosed method can comprise pre-treating the subject's hands. In an aspect, a subject can apply a liquid skin cleanser (e.g., Hibiclens) to his hands. Using water, the subject can wash his hands with the Hibiclens for at least 5 seconds, at least 10 seconds, at least 15 seconds, at least 20 seconds, or at least 30 seconds.

In an aspect, a disclosed method can comprise repeating the applying step until the bacterial infection, suspected bacterial infection, the fungal infection, or the suspected fungal infection is eradicated or appears to be eradicated. In an aspect, a disclosed method can comprise repeating the applying step twice daily until the bacterial infection, suspected bacterial infection, the fungal infection, or the suspected fungal infection is eradicated or appears to be eradicated. In an aspect, a disclosed method can comprise repeating the applying step twice daily for a pre-determined amount of time. In an aspect, the pre-determined amount of time can comprise at least 5 days, at least 7 days, at least 10 days, at least 14 days, at least 21 days, at least 30 days, or more than 30 days. In an aspect, the pre-determined amount can comprise an amount of time lasting at least 5-7 days, at least 7-10 days, at least 10-14 days, at least 14-21 days, at least 21-30 days, at least 30 days, or more than 30 days.

In an aspect, applying the compounded composition can comprise contacting the compounded composition with the subject's skin until the compounded composition has been absorbed or substantially absorbed by the skin. In an aspect, applying can comprise using a sterile applicator to contact the compounded composition with the skin. In an aspect, applying can comprise contacting about 2 g to about 6 g, or about 3 g to about 5 g, or about 4 g of the compounded composition with the subject's skin. In an aspect, a disclosed compounded composition can be applied to skin in conjunction with an occlusive dressing. In an aspect, a disclosed method can comprise applying a covering to the skin affected by the infection.

In an aspect, a disclosed compounded composition can be mixed with a diluent to form a solution or suspension and then applied to the subject's skin. Diluents are discussed supra. In an aspect, a disclosed compounded composition and the diluent can be mixed in a mixing container. In an aspect, a mixing container can have a pre-determined size that can measure or hold a pre-determined amount or volume. In an aspect, a mixing container can measure or hold about 30 mL to about 300 mL. In an aspect, the mixing container can hold about 30 mL, about 60 mL, about 90 mL, about 120 mL, about 150 mL, about 180 mL, about 210 mL, about 240 mL, about 270 mL, or about 300 mL. In an aspect, the mixing container can hold about 180 mL. In an aspect, a disclosed method can comprise cleaning and drying a mixing container.

In an aspect, a disclosed compounded composition can be applied to the subject's skin as a dry powder or as an ointment. In an aspect, a disclosed compounded composition can be applied to the subject's skin as a cream, or lotion, or emulsion, or gel. For example, the compounded composition may comprise a compounded ointment of any disclosed compounded composition formulated in an ointment as described herein.

In one embodiment, a method of treating an infection comprises applying to infected skin a compounded composition ointment comprising a therapeutically effective amount of mupirocin ointment (e.g., mupirocin 2% ointment) and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof. All or a portion of the antibacterial agent may comprise anti-infective for injection powder compounded with the mupirocin ointment. In this or another embodiment, a method of treating an infection comprises applying to infected skin a compounded composition comprising a therapeutically effective amount of a compounded composition comprising streptomycin alone or in combination with one or more additional anti-infectives as described. In one example, one or more additional anti-infectives may comprise colistimethate, clindamycin, mupirocin, levofloxacin, or combination thereof. All or a portion of the streptomycin and anti-infectives may be obtained from anti-infective for injection powders, tablets, or bulk powders. The compounded composition may be in various formats such as a dry powder, cream, ointment, emulsion (o/w, w/o), gel, jelly, wax, solution. Solutions may include, for example, water (e.g., potable water, sterile water, water for injection), aqueous based solutions, oil based solutions, organic solvent based solutions, saline solutions (e.g., 0.9% saline, normal saline), povidone iodine solutions, sodium hypochlorite solution (Dakin's solution), hydrogen peroxide solutions, or cleansers (e.g., wound cleansers).

In various embodiments, a method of making of treating an infection of suspected infection with a compounded composition described herein comprising a dry powder, topical solution, or other compounded topical formulation includes formulating the composition to include an amount of streptomycin configured to provide less than or equal to 1 gm of delivered streptomycin per day, such as less than about 25 mg, about 50 mg, about 75 mg, about 100 mg, about 200 mg, about 300 mg, about 400 mg, about 500 mg, about 600 mg, about 700 mg, about 800 mg, or about 900 mg. For example, the strength of a compounded composition for topical administration with respect to streptomycin and amount to be administered may be determined by the amount of streptomycin that may be delivered using the desired format and number of treatments per day. Accordingly, a method of treating and infection or suspected infection may include combining a suitable amount of diluent to formulate the compounded composition for administration and/or administering a suitable amount of compounded composition to deliver between 25 mg and 1 gm of streptomycin per day. Thus, according to at least one embodiment, the compounded composition may be formulated such that it may be contacted with a body surface of a subject that is infected or suspected to be infected with a suitable amount of the compounded composition to topically deliver between 25 mg and 1 gm of streptomycin per day, such as between about 25 mg and about 900 mg, about 25 mg and about 500 mg, about 25 mg and about 200 mg, about 50 mg and about 1 gm, about 50 mg and about 800 mg, about 50 mg and about 500 mg, about 50 mg and about 200 mg, about 100 mg and about 1 gm, about 100 mg and about 800 mg, about 100 mg and about 500 mg, about 300 mg and about 1 gm, about 300 mg and about 800 mg, about 300 mg and about 500 mg. about 500 mg and about 1 gm, about 500 mg and about 800 mg, or about 800 mg and about 1 gm. Accordingly, streptomycin and one or more additional anti-infectives, when present, may be compounded with or mixed with a suitable amount of diluent to formulate the compounded composition for administration. The ratio of second anti-infective agent, when present, to streptomycin in a compounded composition, which may include compounded capsules, compounded ointments, compounded topical compositions obtained by mixing a compounded composition, such as a compounded capsule or compounded ointment, with a diluent at the time of administration, may be about 1:1, about 1:2, about 1:3, about 1:4, about 1:5, about 1:6, about 1:7, about 1:8, about 1:9, about 1:10, about 1:12, about 1:14, about 1:15, about 1:20, or less. In various embodiments, the ratio of the second anti-infective agent to the first anti-infective agent is between about 1:1 and 1:20, 1:2 and about 1:15, about 1:3 and about 1:15, about 1:3 and about 1:10, about 1:4 and about 1:15, or about 1:4 and about 1:10.

In an aspect, the subject can be diagnosed with or can be suspected of having a bacterial infection or a fungal infection that affects the subject's skin. In an aspect, the subject can have diabetes, can be obese, can be immunocompromised, can be non-ambulatory, or can have poor blood flow, or a combination thereof. In an aspect, the subject can routinely wear thick socks or wear heavy boots.

In an aspect, a disclosed method can comprise preparing a disclosed compounded composition. Disclosed and discussed supra are methods of preparing a disclosed compounded composition, such as, for example, wherein the compounded composition comprises (1) a therapeutically effective amount of a first antibacterial agent and a therapeutically effective amount of a second antibacterial agent, (2) a therapeutically effective amount of an antibacterial agent and a therapeutically effective amount of an antifungal agent, (3) a therapeutically effective amount of a first antibacterial agent, a therapeutically effective amount of a second antibacterial agent, and a therapeutically effective amount of an antifungal agent, (4) a therapeutically effective amount of mupirocin and a therapeutically effective amount of an antibacterial agent, (5) a therapeutically effective amount of mupirocin and a therapeutically effective amount of tobramycin or a pharmaceutically acceptable salt thereof, (6) a therapeutically effective amount of mupirocin and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof, (8) a therapeutically effective amount of streptomycin and a therapeutically effective amount of an additional anti-infective, (9) a therapeutically effective amount of streptomycin and a therapeutically effective amount of an additional anti-infective comprising colistimethate, clindamycin, mupirocin, levofloxacin, or combination thereof.

In an aspect, a disclosed method of treating or preventing an infection can comprise modifying one or more aspect of the disclosed method. For example, in an aspect, a disclosed method can comprise changing or altering the amount of the disclosed compounded composition applied to a subject's skin, or by changing the frequency of the subject's use of the compounded composition, or by changing the duration of time that the subject uses the compounded composition, or by substituting one compounded composition for another compounded composition, or a combination thereof.

F. Methods of Treating or Preventing a Foot Infection Using a Compounded Composition Disclosed herein is a method of treating or preventing a foot infection, the method comprising: (i) adding a compounded composition to water contained within a foot bath; (ii) agitating the water contained within the foot bath; and (iii) contacting the agitated water with at least a part of one or both feet of a subject.

Disclosed herein is a method of treating or preventing a foot infection, the method comprising: (i) agitating water contained within a foot bath; (ii) adding a compounded composition to the water contained with the foot bath; and (iii) contacting the agitated water with at least a part of one or both feet of a subject.

Disclosed herein is a method of treating or preventing a foot infection, the method comprising: (i) mixing a compounded composition with a diluent to create a solution or suspension; (ii) adding the solution or suspension to water contained within a foot bath; (iii) agitating the water contained within the foot bath; and (iv) contacting the agitated water with at least part of one or both feet of a subject.

Disclosed herein is a method of treating or preventing a foot infection, the method comprising: (i) mixing a compounded composition with a diluent to create a solution or suspension; (ii) agitating water contained within a foot bath; (iii) adding the solution or suspension to the water contained within the foot bath; and (iv) contacting the agitated water with at least part of one or both feet of a subject.

Disclosed herein is a method of treating or preventing a foot infection, the method comprising: (i) adding a compounded composition to water contained within a foot bath; (ii) agitating the water contained within the foot bath; and (iii) contacting the agitated water with at least a part of one or both feet of a subject, wherein the compounded composition comprises (1) a therapeutically effective amount of a first antibacterial agent and a therapeutically effective amount of a second antibacterial agent, (2) a therapeutically effective amount of an antibacterial agent and a therapeutically effective amount of an antifungal agent, (3) a therapeutically effective amount of a first antibacterial agent, a therapeutically effective amount of a second antibacterial agent, and a therapeutically effective amount of an antifungal agent, (4) a therapeutically effective amount of mupirocin and a therapeutically effective amount of an antibacterial agent, (5) a therapeutically effective amount of mupirocin and a therapeutically effective amount of tobramycin or a pharmaceutically acceptable salt thereof, (6) a therapeutically effective amount of mupirocin and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof, (8) a therapeutically effective amount of streptomycin and a therapeutically effective amount of an additional anti-infective, (9) a therapeutically effective amount of streptomycin and a therapeutically effective amount of an additional anti-infective comprising colistimethate, clindamycin, mupirocin, levofloxacin, or combination thereof.

Disclosed herein is a method of treating or preventing a foot infection, the method comprising: (i) agitating water contained within a foot bath; (ii) adding a compounded composition to the water contained within the foot bath; and (iii) contacting the agitated water with at least a part of one or both feet of a subject. The compounded composition may be any compounded composition, e.g., compounded ointment, described herein.

Disclosed herein is a method of treating or preventing a foot infection, the method comprising: (i) mixing a compounded composition with a diluent to create a solution or suspension; (ii) adding the solution or suspension to water contained within a foot bath; (iii) agitating the water contained within the foot bath; and (iv) contacting the agitated water with at least part of one or both feet of a subject, wherein the compounded composition comprises (1) a therapeutically effective amount of a first antibacterial agent and a therapeutically effective amount of a second antibacterial agent, (2) a therapeutically effective amount of an antibacterial agent and a therapeutically effective amount of an antifungal agent, (3) a therapeutically effective amount of a first antibacterial agent, a therapeutically effective amount of a second antibacterial agent, and a therapeutically effective amount of an antifungal agent, (4) a therapeutically effective amount of mupirocin and a therapeutically effective amount of an antibacterial agent, (5) a therapeutically effective amount of mupirocin and a therapeutically effective amount of tobramycin or a pharmaceutically acceptable salt thereof, (6) a therapeutically effective amount of mupirocin and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof, (8) a therapeutically effective amount of streptomycin and a therapeutically effective amount of an additional anti-infective, (9) a therapeutically effective amount of streptomycin and a therapeutically effective amount of an additional anti-infective comprising colistimethate, clindamycin, mupirocin, levofloxacin, or combination thereof.

Disclosed herein is a method of treating or preventing a foot infection, the method comprising: (i) mixing a compounded composition with a diluent to create a solution or suspension; (ii) agitating water contained within a foot bath; (iii) adding the solution or suspension to the water contained within the foot bath; and (iv) contacting the agitated water with at least part of one or both feet of a subject, wherein the compounded composition comprises (1) a therapeutically effective amount of a first antibacterial agent and a therapeutically effective amount of a second antibacterial agent, (2) a therapeutically effective amount of an antibacterial agent and a therapeutically effective amount of an antifungal agent, (3) a therapeutically effective amount of a first antibacterial agent, a therapeutically effective amount of a second antibacterial agent, and a therapeutically effective amount of an antifungal agent, (4) a therapeutically effective amount of mupirocin and a therapeutically effective amount of an antibacterial agent, (5) a therapeutically effective amount of mupirocin and a therapeutically effective amount of tobramycin or a pharmaceutically acceptable salt thereof, (6) a therapeutically effective amount of mupirocin and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof, (8) a therapeutically effective amount of streptomycin and a therapeutically effective amount of an additional anti-infective, (9) a therapeutically effective amount of streptomycin and a therapeutically effective amount of an additional anti-infective comprising colistimethate, clindamycin, mupirocin, levofloxacin, or combination thereof.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

In an aspect, the subject can have diabetes, can be obese, can be immunocompromised, can be non-ambulatory, or can have poor blood flow, or a combination thereof. In an aspect, the subject can routinely wear thick socks or wear heavy boots. In an aspect, the subject has been diagnosed with or is suspected of having a bacterial infection that affects at least part of one or both feet. In an aspect, the subject has been diagnosed with or is suspected of having a bacterial infection and a fungal infection that affect at least part of one or both feet. In an aspect, the subject has been diagnosed with or is suspected of having a fungal infection that affects at least part of one or both feet.

In an aspect, a disclosed method can comprise orally administering to the subject a pharmaceutical composition comprising one or more anti-infective agents. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra.

In an aspect, adding a disclosed compounded composition to the water contained within a foot bath can comprise adding to the water between about 10 g to about 40 g of a disclosed compounded composition, or about 20 g to about 30 g of a disclosed compounded composition, or about 25 g of a disclosed compounded composition.

In an aspect, a disclosed compounded composition and the diluent can be mixed in a mixing container. In an aspect, a mixing container can have a pre-determined size that can measure or hold a pre-determined amount or volume. In an aspect, a mixing container can measure or hold about 30 mL to about 300 mL. In an aspect, the mixing container can hold about 30 mL, about 60 mL, about 90 mL, about 120 mL, about 150 mL, about 180 mL, about 210 mL, about 240 mL, about 270 mL, or about 300 mL. In an aspect, the mixing container can hold about 180 mL.

In an aspect, a disclosed method can comprise adding the diluent to the water contained in the foot bath. In an aspect, the diluent can comprise sodium hypochlorite. In an aspect, the diluent can comprise Dakin's solution. In an aspect, the amount of diluent can be about 20 mL to about 60 mL, or about 30 to about 50 mL, or about 20 mL, or about 30 mL, or about 40 mL, or about 50 mL, or about 60 mL.

In an aspect, adding the solution or suspension comprising the compounded composition and the diluent can be added to the foot bath already having water, thereby increasing the water level in the foot bath.

In an aspect, a disclosed method can comprise heating the water contained within the foot bath. In an aspect, a disclosed method can comprise agitating the water contained within the foot bath. In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the compounded composition, the diluent, or the solution or suspension comprising the compounded composition and the diluent throughout the water contained within the foot bath. Heating agents and/or means to heat water in a compartment are known to the art.

In an aspect of a disclosed method, a disclosed compound composition can be added to the water contained within the foot bath while the water is being heated. In an aspect of a disclosed method, a disclosed compound composition can be added to the water contained within the foot bath while the water is being agitated.

In an aspect, agitation can ensure dissolution of the compounded composition or the dissolution of solution or suspension comprising the compounded composition.

In an aspect, agitation can ensure optimal contact of the compounded composition with at least a part of the subject's foot or feet.

In an aspect, a disclosed method can comprise repeating daily steps (i)-(iii) or steps (i)-(iv). In an aspect, a disclosed method can comprise repeating daily steps (i)-(iii) or steps (i)-(iv) until the bacterial infection, suspected bacterial infection, the fungal infection, or the suspected fungal infection is eradicated or appears to be eradicated. In an aspect, a disclosed method can comprise repeating twice daily the applying step for a pre-determined amount of time. In an aspect, the pre-determined amount of time can comprise at least 5 days, at least 7 days, at least 10 days, at least 14 days, at least 21 days, at least 30 days, or more. In an aspect, the pre-determined amount can comprise an amount of time lasting at least 5-7 days, at least 7-10 days, at least 10-14 days, at least 14-21 days, at least 21-30 days, or at least 30 days.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise removing the compounded composition from a container, such as, for example, a tube, a packet, a capsule, a syringe, a vial, etc., prior to adding the compounded composition to the water. In an aspect, the method can comprise removing the compounded composition from a container, such as, for example, a tube, a packet, a capsule, a syringe, a vial, etc., prior to adding the composition to the diluent. In an aspect, a capsule can be broken apart and the contents of the capsule can be added to the water in the foot bath. In an aspect, an intact capsule can be added to the water in the foot bath.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can comprise preparing a disclosed compounded composition. Methods of preparing a disclosed compounded composition are discussed supra.

In an aspect, a disclosed method of treating or preventing a foot infection can comprise modifying one or more aspect of the disclosed method. For example, in an aspect, a method can be altered by changing the amount of a disclosed compounded composition added to a foot bath, by changing the frequency of the subject's use of the foot bath, or by changing the duration of time that the subject's foot or feet contact the water contained within the foot bath, or by substituting one disclosed compounded composition for another disclosed compounded composition, or a combination thereof.

In various aspects, a method of treating or preventing an infection, such as a foot infection, may comprise making or administering any of the disclosed compounded compositions to an affected skin surface of a subject. In some aspects, the compounded composition comprises a foot bath composition for application to a foot of a subject. In one aspect, any of the disclosed compounded compositions may be administered in a foot bath solution. For example, added into a mixing container along with a suitable amount of diluent.

The composition may be provided in a syringe, for example, for ease of addition with the diluent. The contents (e.g., 25 g) may be added to a suitable amount of diluent, as described herein, and mixed, e.g., in a mixing container. The amount of diluent may be about 15 ml diluent per tablespoon of the ointment. Other ratios may be used, e.g., between about 10 ml and about 50 ml, about 10 ml and about 40 ml, about 10 ml and about 30 ml, about 10 ml and about 20 ml, about 10 ml and about 15 ml, about 15 ml and about 50 ml, about 15 ml and about 40 ml, about 15 ml and about 30 ml, about 10 ml and about 25 ml, about 15 ml and about 20 ml, about 20 ml and about 50 ml, about 20 ml and about 40 ml, about 20 ml and about 30 ml, or about 20 ml and about 25 ml. Furthermore, the compounded composition ointment may be formulated with higher or lower concentrations of actives in the ointment and amounts of the compounded composition ointment added to diluent for administration may thereby adjusted accordingly. Mixing may include shaking or stirring to form a foot bath solution. In a further aspect, the foot bath solution may be further agitated. In one aspect, the mixing container comprises a foot bath. In another aspect, the contents of the mixing container may be added to a foot bath. Administering the foot bath solution may include placement of the foot (or feet) to be treated into the solution. The foot or portion to be treated thereof may be soaked, e.g., submerged, in the bath for a suitable period of time, e.g., between about 5 minutes and about 25 minutes, between about 5 minutes and about 20 minutes, about 5 minutes and about 15 minutes, about 5 minutes and about 10 minutes, between about 10 minutes and about 25 minutes, about 10 minutes and about 20 minutes, about 10 minutes and about 15 minutes, between about 15 minutes and about 25 minutes, about 15 minutes and about 20 minutes, or about 20 minutes and about 25 minutes. Administration may be repeated as directed, e.g., once daily.

In various aspects, the method of treating or preventing a foot infection may include making or administering any of the above foot bath compositions or solutions to a subject and further dispensing or administering up to about 2 g urea 40% cream or equivalent thereof to the affected area two times daily as directed (up to about 4 g per day) and applying up to about 4 g fluocinonide 0.1% cream to the affected area two times daily as directed (up to about 8 g per day). In another aspect, the method of treating or preventing a foot infection may include making or administering any of the above foot bath compositions or solutions to a subject and further dispensing or administering up to about 2 g urea 40% cream or equivalent thereof to the affected area two times daily as directed (up to about 4 g per day) and applying up to about 3 g of clobetasol 0.05% ointment to the affected area two times daily as directed (up to about 6 g per day).

In various aspects, the method of treating or preventing an infection, such as a foot infection, may include making or administering any of the above foot bath compositions or solutions to a subject and further dispensing or administering up to about 2 g urea 40% cream or equivalent thereof to the affected area two times daily as directed (up to about 4 g per day) and applying up to about 4 g fluocinonide 0.1% cream to the affected area two times daily as directed (up to about 8 g per day). In another aspect, the method of treating or preventing a foot infection may include making or administering any of the above foot bath compositions or solutions to a subject and further dispensing or administering up to about 2 g urea 40% cream or equivalent thereof to the affected area two times daily as directed (up to about 4 g per day) and applying up to about 3 g of clobetasol 0.05% ointment to the affected area two times daily as directed (up to about 6 g per day).

In one aspect, a method of treating or preventing a foot infection, such as a foot infection, may comprise making or administering any of the above foot bath compositions or solutions. In one example, the contents of a capsule may be added to a mixing container along with a suitable amount of diluent. The contents may be mixed, e.g., shaken or stirred, to form a foot bath solution. In a further aspect, the foot bath solution may be further agitated. In one aspect, the mixing container comprises a foot bath. In another aspect, the contents of the mixing container may be added to a foot bath. Administering the foot bath solution may include placement of the foot (or feet) to be treated into the solution. The foot or portion to be treated thereof may be soaked, e.g., submerged, in the bath for a suitable period of time, e.g., between about 5 minutes and about 25 minutes, between about 5 minutes and about 20 minutes, about 5 minutes and about 15 minutes, about 5 minutes and about 10 minutes, between about 10 minutes and about 25 minutes, about 10 minutes and about 20 minutes, about 10 minutes and about 15 minutes, between about 15 minutes and about 25 minutes, about 15 minutes and about 20 minutes, or about 20 minutes and about 25 minutes. Administration may be repeated as directed, e.g., once daily.

In various aspects, the method of treating or preventing and infection, such as a foot infection, may include making or administering any of the above foot bath compositions or solutions to a subject and further dispensing or administering up to about 2 g urea 40% cream or equivalent thereof to the affected area two times daily as directed (up to about 4 g per day) and applying up to about 4 g fluocinonide 0.1% cream to the affected area two times daily as directed (up to about 8 g per day). In another aspect, the method of treating or preventing a foot infection may include making or administering any of the above foot bath compositions or solutions to a subject and further dispensing or administering up to about 2 g urea 40% cream or equivalent thereof to the affected area two times daily as directed (up to about 4 g per day) and applying up to about 3 g of clobetasol 0.05% ointment to the affected area two times daily as directed (up to about 6 g per day).

G. Methods of Treating or Preventing an Infection Using an Intranasally Administered Compounded Composition Disclosed herein is a method of treating or preventing an infection, the method comprising: (i) intranasally administering to a subject a solution or suspension comprising a compounded composition. Disclosed herein is a method of treating or preventing an infection, the method comprising: (i) mixing a compounded composition with a diluent to create a solution or suspension; and (ii) intranasally administering to a subject the solution or suspension.

Disclosed herein is a method of treating or preventing an infection, the method comprising: (i) intranasally administering to a subject a solution or suspension comprising a compounded composition, wherein the compounded composition comprises (1) a therapeutically effective amount of a first antibacterial agent and a therapeutically effective amount of a second antibacterial agent, (2) a therapeutically effective amount of an antibacterial agent and a therapeutically effective amount of an antifungal agent, (3) a therapeutically effective amount of a first antibacterial agent, a therapeutically effective amount of a second antibacterial agent, and a therapeutically effective amount of an antifungal agent, (4) a therapeutically effective amount of mupirocin and a therapeutically effective amount of an antibacterial agent, (5) a therapeutically effective amount of mupirocin and a therapeutically effective amount of tobramycin or a pharmaceutically acceptable salt thereof, (6) a therapeutically effective amount of mupirocin and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof, (8) a therapeutically effective amount of streptomycin and a therapeutically effective amount of an additional anti-infective, (9) a therapeutically effective amount of streptomycin and a therapeutically effective amount of an additional anti-infective comprising colistimethate, clindamycin, mupirocin, levofloxacin, or combination thereof.

Disclosed herein is a method of treating or preventing an infection, the method comprising: (i) mixing a compounded composition with a diluent to create a solution or suspension; and (ii) intranasally administering to a subject the solution or suspension, wherein the compounded composition comprises (1) a therapeutically effective amount of a first antibacterial agent and a therapeutically effective amount of a second antibacterial agent, (2) a therapeutically effective amount of an antibacterial agent and a therapeutically effective amount of an antifungal agent, (3) a therapeutically effective amount of a first antibacterial agent, a therapeutically effective amount of a second antibacterial agent, and a therapeutically effective amount of an antifungal agent, (4) a therapeutically effective amount of mupirocin and a therapeutically effective amount of an antibacterial agent, (5) a therapeutically effective amount of mupirocin and a therapeutically effective amount of tobramycin or a pharmaceutically acceptable salt thereof, (6) a therapeutically effective amount of mupirocin and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof, (8) a therapeutically effective amount of streptomycin and a therapeutically effective amount of an additional anti-infective, (9) a therapeutically effective amount of streptomycin and a therapeutically effective amount of an additional anti-infective comprising colistimethate, clindamycin, mupirocin, levofloxacin, or combination thereof.

In an aspect, the subject can have diabetes, can be obese, can be immunocompromised, can be non-ambulatory, or can have poor blood flow, or a combination thereof. In an aspect, the subject has been diagnosed with or can be suspected of having (i) cancer that affects at least a part of the respiratory tract, (ii) emphysema, (iii) pneumonia, (iv) bronchitis, (v) tuberculosis, (vi) asthma, or (vii) a combination thereof. In an aspect, the subject has been diagnosed with or is suspected of having a bacterial infection that affects at least a part of the subject's respiratory tract or a respiratory organ. In an aspect, the subject has been diagnosed with or is suspected of having a bacterial infection and a fungal infection that affect at least a part of the subject's respiratory tract or a respiratory organ. In an aspect, the subject has been diagnosed with or is suspected of having a fungal infection that affects at least one part of the subject's respiratory tract or a respiratory organ.

In an aspect, a disclosed method can comprise orally administering to the subject a pharmaceutical composition comprising one or more anti-infective agents. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra.

In an aspect, mixing the compounded composition with the diluent can comprise adding about 1 g to about 30 g of the compounded composition to the diluent. In an aspect, mixing the compounded composition with the diluent can comprise adding about 1 g, or about 5 g, or about 10 g, or about 15 g, or about 20 g, or about 25 g, or about 30 g of the compounded composition to the diluent. In an aspect, mixing the compounded composition to the diluent can comprise adding about 10 g and about 20 g, about 15 g and about 30 g, about 20 g and about 30 g, or about 22 g and about 27 g of the compounded composition with the diluent.

In an aspect, a disclosed compounded composition and the diluent can be mixed in a mixing container. In an aspect, a mixing container can have a pre-determined size that can measure or hold a pre-determined amount or volume. In an aspect, a mixing container can measure or hold about 30 mL to about 300 mL. In an aspect, the mixing container can hold about 30 mL, about 60 mL, about 90 mL, about 120 mL, about 150 mL, about 180 mL, about 210 mL, about 240 mL, about 270 mL, or about 300 mL. In an aspect, the mixing container can hold about 180 mL.

In an aspect, the diluent can comprise sodium hypochlorite. In an aspect, the diluent can comprise Dakin's solution. In an aspect, the amount of diluent can be about 20 mL to about 60 mL, or about 30 to about 50 mL, or about 20 mL, or about 30 mL, or about 40 mL, or about 50 mL, or about 60 mL.

In an aspect, a disclosed method can comprise repeating daily the administering step. In an aspect, a disclosed method can comprise repeating daily the administering step until the bacterial infection or suspected bacterial infection or the fungal infection or the suspected fungal infection is eradicated or appears to be eradicated.

In an aspect, a disclosed method can comprise repeating daily the mixing step or the administering step or repeating both steps. In an aspect, a disclosed method can comprise repeating daily the mixing step or the administering step or reporting both the steps until the bacterial infection, suspected bacterial infection, the fungal infection, or the suspected fungal infection is eradicated or appears to be eradicated.

In an aspect, a disclosed method can comprise repeating the mixing step or the administering step or both the mixing step and the administering step for a pre-determined amount of time. In an aspect, the pre-determined amount of time can comprise at least 5 days, at least 7 days, at least 10 days, at least 14 days, at least 21 days, at least 30 days, or more. In an aspect, the pre-determined amount can comprise an amount of time lasting at least 5-7 days, at least 7-10 days, at least 10-14 days, at least 14-21 days, at least 21-30 days, or at least 30 days.

In an aspect, intranasally administering can comprise delivering to the subject the solution or suspension via the subject's nares. In an aspect, delivering the solution or suspension to the nares can comprise using irrigation, or using a nasal spray, or using a metered inhaler, or using nebulization, or using particle dispersion. In an aspect, delivering the solution or suspension can comprise a sinus rinse, which can use positive pressure to clean or irrigate the nasal passages and maintain the head of the subject in an upright position. A sinus rinse delivery device known to the art is the NeilMed® device. The art is familiar with each of these techniques, the equipment required to effect each of these techniques, and the means to prepare the compounded composition for each technique of intranasal administration.

In an aspect, a small particle nebulization delivery system can be configured to nebulize the solution or suspension comprising a disclosed compounded composition to produce small particles or droplets. In an aspect, small particles or droplets can have aerosol characteristics, wherein the particle size of the majority (e.g., at least 50%, at least 60%, at least 70%, at least 80%, at least 90%, or more) of the particles or droplets formed by the nebulization can be less than about 10 microns, or less than about 8 microns, or less than about 5 microns, or less than about 3 microns. In an aspect, the particles or droplets can be about 3-about 10 microns, or about 3 microns-about 8 microns, or about 3 microns-about 5 microns, or about 5 microns-about 8 microns, or about 5 microns-about 10 microns, or about 8 microns-about 10 microns.

In an aspect, a large particle nebulization delivery system can be configured to nebulize the solution or suspension comprising a disclosed compounded composition to produce large particles or droplets. In an aspect, small particles or droplets can have aerosol characteristics, wherein the particle size of the majority (e.g., at least 50%, at least 60%, at least 70%, at least 80%, at least 90%, or more) of the particles or droplets formed by the nebulization can be more than about 10 microns, or more than about 15 microns, or more than about 20 microns, or more than about 25 microns. In an aspect, the particles or droplet can be about 10 microns-about 25 microns, or about 10 microns-about 20 microns, or about 10 microns-about 15 microns, or about 15 microns-about 25 microns, or about 15 microns-about 20 microns, or about 20 microns-about 25 microns.

In an aspect, a disclosed method can comprise cleaning the device.

In an aspect, a disclosed method can comprise preparing a compounded composition. Methods of preparing a disclosed compounded composition are discussed supra.

In an aspect, a disclosed method of treating or preventing an infection using an intranasally administered compounded composition can comprise modifying one or more aspect of the disclosed method. For example, in an aspect, a method can be modified by changing the amount of a disclosed compounded composition intranasally administered, by changing the frequency of the subject's use of intranasal administration, or by substituting one disclosed compounded composition for another disclosed compounded composition, or a combination thereof.

What is claimed is:

1. A method of treating a bacterial foot infection of a human subject, the method comprising:
   formulating a treatment composition comprising combining an aqueous diluent and a dry powder comprising one or more anti-infective agents, wherein the dry powder comprises at least a first anti-infective agent comprising streptomycin or a pharmaceutically acceptable salt thereof; and
   contacting, in a foot bath, a foot surface of a subject that is infected or suspected to be infected with the treatment composition to topically deliver the one or more anti-infective agents to the foot surface.

2. The method of claim 1, wherein the one or more anti-infective agents comprise a second anti-infective agent comprising colistimethate, clindamycin, mupirocin, levofloxacin, or combination thereof.

3. The method of claim 2, wherein formulating the treatment composition further comprises opening a capsule comprising at least the first anti-infective agent to release the dry powder of at least the first anti-infective agent for combining with the diluent.

4. The method of claim 3, wherein the dry powder contained in the capsule comprises both the first anti-infective agent and the second anti-infective agent.

5. The method of claim 1, wherein the compounded composition comprises between about 1% and about 10% streptomycin by weight.

6. The method of claim 1, wherein the contacting the body surface comprises contacting the body surface with a suitable amount of the treatment composition to topically deliver between 25 mg and 1 gm of streptomycin per day.

7. The method of claim 2, wherein the second anti-infective agent is present in the dry powder at a ratio between about 1:3 and about 1:10 with respect to the first anti-infective agent.

8. The method of claim 2, wherein combining the diluent and dry powder comprises combining a dry powder of streptomycin sulfate with the diluent.

9. The method of claim 1, wherein formulating the treatment composition further comprises combining an additional anti-infective agent comprising a mupirocin ointment with the dry powder and diluent.

* * * * *